(12) United States Patent
Ortoleva

(10) Patent No.: US 9,652,596 B2
(45) Date of Patent: May 16, 2017

(54) DEDUCTIVE MULTISCALE SIMULATION USING ORDER PARAMETERS

(75) Inventor: Peter J. Ortoleva, Bloomington, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 759 days.

(21) Appl. No.: 13/976,536

(22) PCT Filed: Jan. 7, 2012

(86) PCT No.: PCT/US2012/020569
§ 371 (c)(1),
(2), (4) Date: Jun. 27, 2013

(87) PCT Pub. No.: WO2012/094655
PCT Pub. Date: Jul. 12, 2012

(65) Prior Publication Data
US 2013/0275094 A1    Oct. 17, 2013

Related U.S. Application Data

(60) Provisional application No. 61/430,673, filed on Jan. 7, 2011.

(51) Int. Cl.
G06G 7/48 (2006.01)
G06G 7/58 (2006.01)
G06F 19/00 (2011.01)
G06F 19/16 (2011.01)

(52) U.S. Cl.
CPC ........... *G06F 19/701* (2013.01); *G06F 19/16* (2013.01)

(58) Field of Classification Search
CPC .............................. G06F 19/701; G06F 19/16
USPC ................................ 703/1, 6, 11–12; 702/27
See application file for complete search history.

(56) References Cited

U.S. PATENT DOCUMENTS

| 5,553,004 A | 9/1996 | Ronbech-Jensen et al. |
| 6,125,235 A * | 9/2000 | Padilla .................. G06F 19/708 703/11 |
| 2002/0013687 A1 | 1/2002 | Ortoleva |
| 2006/0160136 A1 * | 7/2006 | Xiang .................. G01N 24/087 435/7.1 |

(Continued)

OTHER PUBLICATIONS

PCT International Search Report issued in connection with PCT/US2012/020569 and completed by the U.S. Searching Authority on Apr. 18, 2012.

(Continued)

*Primary Examiner* — Eunhee Kim
(74) *Attorney, Agent, or Firm* — Barnes & Thornburg LLP

(57) ABSTRACT

Illustrative embodiments of systems and methods for the deductive multiscale simulation of macromolecules are disclosed. In one illustrative embodiment, a deductive multiscale simulation method may include (i) constructing a set of order parameters that model one or more structural characteristics of a macromolecule, (ii) simulating an ensemble of atomistic configurations for the macromolecule using instantaneous values of the set of order parameters, (iii) simulating thermal-average forces and diffusivities for the ensemble of atomistic configurations, and (iv) evolving the set of order parameters via Langevin dynamics using the thermal-average forces and diffusivities.

16 Claims, 15 Drawing Sheets

(56) References Cited

U.S. PATENT DOCUMENTS

2008/0059140 A1    3/2008   Salmon et al.
2008/0147360 A1    6/2008   Fejes et al.
2009/0037159 A1    2/2009   Wen et al.

OTHER PUBLICATIONS

Wu, et al. "Self-Guided Langevin Dynamics Simulation Method" In Chemical Physics Letters, vol. 381, issued 3-4, pp. 512-518 [online]. Published Nov. 2003.

* cited by examiner

DEDUCTIVE MULTISCALE SIMULATION USING ORDER PARAMETERS

CROSS-REFERENCE TO RELATED APPLICATIONS

This application is a U.S. national counterpart application of International Application Ser. No. PCT/US2012/020569, filed Jan. 7, 2012, which claims the benefit of U.S. Provisional Patent Application No. 61/430,673 filed Jan. 7, 2011. The entire disclosures of both of the foregoing applications are hereby incorporated by reference.

STATEMENT REGARDING FEDERALLY SPONSORED RESEARCH

This invention was made with government support under Grant No. CHE-1037383 awarded by the National Science Foundation, under Grant No. EB008951 awarded by the National Institutes of Health (NIBIB), and under Grant No. DE-FG02-05ER25676 awarded by the U.S. Department of Energy. The U.S. Government has certain rights in the invention.

TECHNICAL FIELD

The present invention relates generally to deductive multiscale simulations of macromolecules and, more particularly, to deductive multiscale simulations of macromolecules using order parameters that model one or more structural characteristics of the macromolecules.

BACKGROUND ART

Microbes such as viruses and bacteria are organized hierarchically. For example, a virus is constituted of atoms assembled into macromolecules which, in turn, constitute several substructures. For a non-enveloped virus, the latter are genetic material and the capsid. For an enveloped system, such as dengue virus, there is an outer protein net, a lipid zone, and an inner RNA-protein complex. Accompanying this hierarchical organization is a spectrum of time and length scales.

Modern nano-characterization experimental methodologies make the development of microbial simulation approaches timely. For example, atomic force microscopy (AFM) may be employed to investigate a range of biological processes from unfolding of a single molecule to nano-indentation of viruses. A standard AFM can scan a sample more than 10 thousand times per second, yielding an ensemble measurement that parallels a statistical mechanical approach. Thus, to model such experiments computationally, a framework is needed that addresses structures in a range of sizes from single macromolecules to viruses and bacteria, without losing information at any time or length scale.

Nano-technical methods for characterizing macromolecular assemblies include AFM, Ion Mobility—Mass Spectrometry, chemical labeling, and nano-pore measurements. While these techniques provide information on structure, they are coarse-grained, in that they do not resolve all-atom configurations. X-ray and electron microscopy provide detailed structure but do not provide information on dynamics. Solid-state nuclear magnetic resonance (NMR) techniques do provide an ensemble of atom-resolved structures but cannot be used to give overall structure for a macromolecular assembly. A method which integrates multiple types of nano-characterization data with a predictive all-atom simulation approach would greatly advance the understanding of microbial systems.

The above and other experimental techniques can be performed under various microenvironmental conditions such as salinity and pH. These variations modulate interactions between solvent accessible parts of the microbe and host medium atoms, inducing structural and functional changes of the former. An all-atom model is often essential to correctly probe these interactions. Structural fluctuations and internal dynamics are a central feature of many biological processes. For example, in the presence of an energy barrier, the atomic fluctuations allow self-organization of lipids in membranes. Fluctuations are also important in expressing the conformational diversity of macromolecules that allows for large deformations upon drug binding. Similarly, excessive fluctuations in viral epitopes appear to diminish immune response and may explain the dependence of immunogenicity on their fluctuations. Thus, an all-atom description is desirable to account for all sources of fluctuation in simulating the aforementioned processes, and hence has been the basis of traditional molecular dynamics (MD) approaches.

All-atom MD simulations of macromolecular assemblies involving more than a million atoms (such as a virus in an explicit solvation environment) require large computational capabilities and have been accomplished using more than 1000 processors for a single time-course. To simulate viruses over microseconds on such a platform would require engaging this many processors for months (assuming the usual femto-second MD timestep). This restricts traditional MD to less than 50 nm structures and hundred nano-second timescales. Hence, incorporating information about atomic processes into microbe modeling has been a challenge. Billion-atom MD simulations have been accomplished. However, these simulations neglect Coulomb interactions, bonded forces, or the rapidly fluctuating proton. All of these are central to biomolecular structure and dynamics.

Multiscale approaches have been developed to address the above computational challenges. As used herein, a "multiscale" method simultaneously accounts for processes on a range of scales. These methods may yield insights into the dynamics of a system as it simultaneously evolves across multiple scales in space and time. Existing approaches to multiscale modeling include Principal Component Analysis (PCA) modes to identify collective behaviors in macromolecular systems, dihedral angles, curvilinear coordinates to characterize macromolecular folding and coiling, bead models wherein a peptide or nucleotide is represented by a bead which interacts with others via a phenomenological force, and spatial coarse-grained models. The foregoing approaches, however, suffer from one or more of the following difficulties: (1) characteristic variables are not slowly varying in time; (2) macromolecular twist is not readily accounted for; (3) their internal dynamics, and hence inelasticity of their collisions is neglected; and (4) the forces involved must be calibrated for most new applications.

DISCLOSURE OF INVENTION

The present invention may comprise one or more of the features recited in the attached claims and/or one or more of the following features and any combinations thereof.

According to one aspect, a deductive multiscale simulation method may comprise (i) constructing a set of order parameters that model one or more structural characteristics of a macromolecule, (ii) simulating an ensemble of atomistic configurations for the macromolecule using instantaneous values of the set of order parameters, (iii) simulating thermal-average forces and diffusivities for the ensemble of atomistic configurations, and (iv) evolving the set of order parameters via Langevin dynamics using the thermal-average forces and diffusivities. The deductive multiscale simulation method may comprise repeating steps (ii)-(iv) at each of a plurality of Langevin timesteps. The plurality of Langevin timesteps may each be between 50 and 100 picoseconds.

In some embodiments, step (i) of the deductive multiscale simulation method may comprise constructing the set of order parameters using an all-atom reference structure for the macromolecule. The deductive multiscale simulation method may further comprise updating the all-atom reference structure to reflect a deformation of the macromolecule. The deductive multiscale simulation method may also comprise adding one or more new order parameters to the set of order parameters in response to the presence of a long-time tail in a correlation function.

In other embodiments, step (ii) of the deductive multiscale simulation method may comprise determining a quasi-equilibrium probability distribution of the ensemble of atomistic configurations following from entropy maximization constrained to the instantaneous values of the set of order parameters. Step (iii) of the deductive multiscale simulation method may comprise determining an interatomic force-field using at least one of Monte Carlo integration and molecular dynamics.

In still other embodiments, the deductive multiscale simulation method may further comprise synthesizing the macromolecule modeled by the set of order parameters. The synthesized macromolecule may comprise a nano-medical system.

According to another aspect, one or more computer readable media may comprise a plurality of instructions which, when executed by one or more processors, cause the one or more processors to (i) construct a set of order parameters that model one or more structural characteristics of a macromolecule, (ii) simulate an ensemble of atomistic configurations for the macromolecule using instantaneous values of the set of order parameters, (iii) simulate thermal-average forces and diffusivities for the ensemble of atomistic configurations, and (iv) evolve the set of order parameters via Langevin dynamics using the thermal-average forces and diffusivities. The plurality of instructions may cause the one or more processors to repeat steps (ii)-(iv) at each of a plurality of Langevin timesteps. The plurality of Langevin timesteps may each be between 50 and 100 picoseconds.

In some embodiments, the plurality of instructions may cause the one or more processors to perform step (i), at least in part, by constructing the set of order parameters using an all-atom reference structure for the macromolecule. The plurality of instructions may further cause the one or more processors to update the all-atom reference structure to reflect a deformation of the macromolecule. The plurality of instructions may also cause the one or more processors to add one or more new order parameters to the set of order parameters in response to the presence of a long-time tail in a correlation function.

In other embodiments, the plurality of instructions may cause the one or more processors to perform step (ii), at least in part, by determining a quasi-equilibrium probability distribution of the ensemble of atomistic configurations following from entropy maximization constrained to the instantaneous values of the set of order parameters. The plurality of instructions may cause the one or more processors to perform step (iii), at least in part, by determining an interatomic force-field using at least one of Monte Carlo integration and molecular dynamics.

BRIEF DESCRIPTION OF DRAWINGS

The detailed description particularly refers to the accompanying figures in which.

BEST MODE(S) FOR CARRYING OUT THE INVENTION

Figure 1:
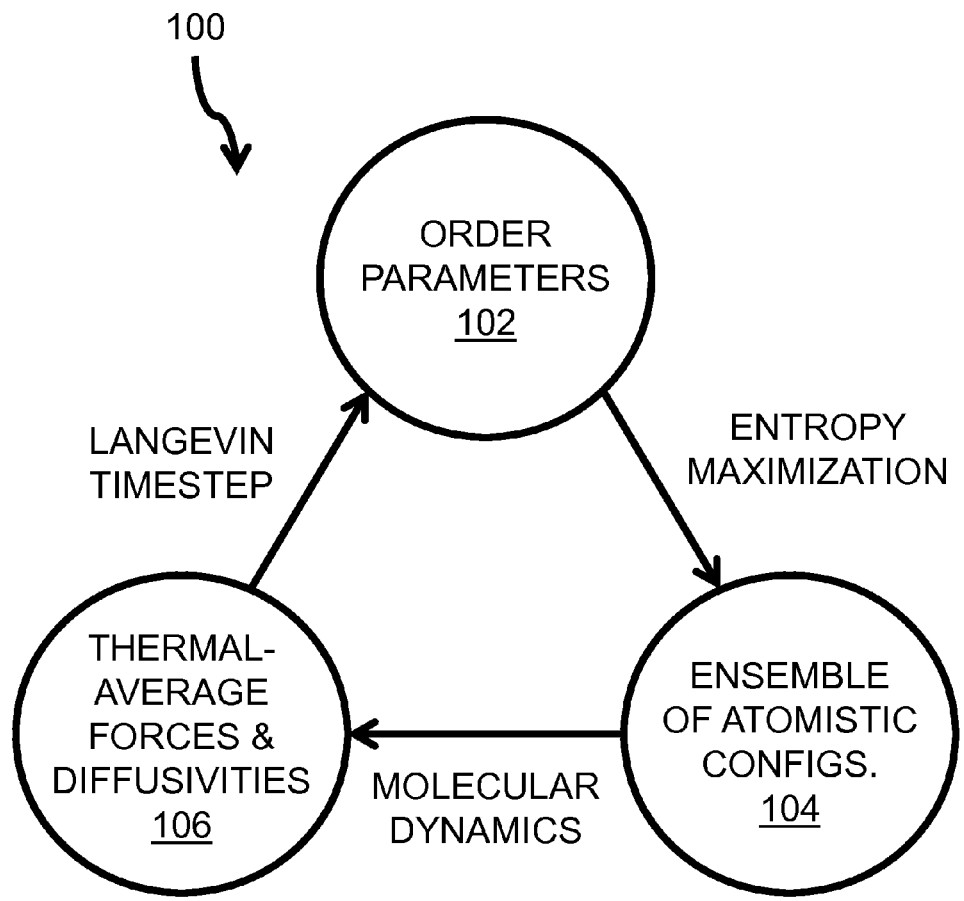
FIG. 1 is a simplified flow diagram illustrating interscale feedback and the information transfer across scales underlying the presently disclosed Deductive Multiscale Simulator (DMS)

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and appended claims.

In the following description, numerous specific details such as logic implementations and logic partitioning/integration choices may be set forth in order to provide a more thorough understanding of the present disclosure. It will be appreciated, however, by one skilled in the art that embodiments of the disclosure may be practiced without such specific details. In other instances, full software instruction sequences have not been shown in detail in order not to obscure the invention. Those of ordinary skill in the art, with the included descriptions, will be able to implement appropriate functionality without undue experimentation.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may be implemented as instructions carried by or stored on one or more machine-readable media, which may be read and executed by one or more processors. A machine-readable medium may be embodied as any device, mechanism, or physical structure for storing or transmitting information in a form readable by a machine (e.g., a computing device). For example, a machine-readable medium may be embodied as read only memory (ROM); random access memory (RAM); magnetic disk storage media; optical storage media; flash memory devices; mini- or micro-SD cards, memory sticks, electrical signals, and others.

In the drawings, specific arrangements or orderings of schematic elements, such as those representing instruction blocks and data elements, may be shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

In general, schematic elements used to represent instruction blocks may be implemented using any suitable form of machine-readable instruction, such as software or firmware applications, programs, functions, modules, routines, processes, procedures, plug-ins, applets, widgets, code fragments, and/or others, and that each such instruction may be implemented using any suitable programming language, library, application programming interface (API), and/or other software development tools. For example, some embodiments may be implemented using Java, C++, and/or other programming languages. Similarly, schematic elements used to represent data or information may be implemented using any suitable electronic arrangement or structure, such as a register, data store, table, record, array, index, hash, map, tree, list, graph, file (of any file type), folder, directory, database, and/or others.

Further, in the drawings, where connecting elements (e.g., solid or dashed lines or arrows) are used to illustrate a connection, relationship, or association between or among two or more schematic elements, the absence of any such connecting elements is not meant to imply that no connection, relationship or association can exist. In other words, some connections, relationships or associations between elements may not be shown in the drawings so as not to obscure the disclosure. In addition, for ease of illustration, a single connecting element may be used to represent multiple connections, relationships, or associations between elements. For example, where a connecting element represents a communication of signals, data, or instructions, it should be understood by those skilled in the art that such element may represent one or multiple signal paths, as may be needed, to effect the communication.

The present disclosure describes a multiscale framework for simulating the dynamics of macromolecules, also referred to as deductive multiscale modeling. As disclosed herein, deductive multiscale modeling is a procedure wherein a coarse-grained model is derived from fine-scale equations. Specifically, factors in the coarse-grained equations may be constructed from information obtained from solving the fine-scale equations. This yields algorithms that account for the two-way transformation between the two scales. In some embodiments, these algorithms may be expanded to more than two scales (e.g., to include multiple levels of coarse-grained variables). These algorithms may be embodied in software as a Deductive Multiscale Simulator (DMS) that may carry out simulations of systems consisting of 103 to 109 atoms, or more. The DMS may use deductive multiscale modeling, an underlying all-atom molecular dynamics model, and an inter-atomic force field to perform simulations in a manner that preserves all-atom resolution and accuracy but is orders of magnitude more computationally efficient than conventional molecular dynamics techniques. In some embodiments, the DMS may be run iteratively as part of a computer-aided design workflow to discover a set of system parameters that maximize an objective function. Among many other uses, the DMS can be used in the discovery and/or design of a number of nanomedical systems, including, but not limited to, vaccine nano-particles, nano-capsules for the targeted delivery of molecular therapeutics, genes, and other nano-medical structures, nano-particles whose surface is functionalized to adhere on the surfaces of targeted tissues for medical imaging, and molecular machines useful in, for example, intracellular surgery. After discovery and/or design using the DMS, a simulated nano-medical system may be synthesized using any suitable method of manufacture.

The dynamics of macromolecules may be divided into high frequency atomic vibrations and slow (coherent) large-spatial-scale conformational changes. A set of order parameters (OPs) may be introduced to describe the coherent, overall structural changes of a macromolecule, while the small amplitude, high frequency atomic fluctuations may be described by an equilibrium distribution following from entropy maximization constrained to instantaneous values of the OPs. In effect, the presently disclosed OPs filter out the high frequency atomistic fluctuations. These concepts may be embodied via a multiscale analysis of the Liouville equation. The result of this analysis is a set of Langevin equations, all factors within which are related to an inter-atomic force-field. This yields a force-field based multiscale algorithm that allows for all-atom simulation of macromolecular structural transitions with high computational efficiency. This computational approach may be employed in fundamental and applied studies of the dynamics of macromolecules, as well as the macromolecules interactions with their micro-environment.

OPs characterize the state of organization of a system. As used herein, OPs are coarse-grained variables characterizing the overall structure and/or spatial organization of a macromolecule. Introducing these OPs provides a dimensionality reduction that arrives at a practical computational algorithm for large systems and reveals the salient features of the structure/dynamics of nano-scale assemblies. The presently disclosed OPs are related to the underlying all-atom description, enabling a unified treatment based on the Newtonian Liouville equation. The present disclosure analyzes an illustrative set of OPs, showing that they facilitate a complete analysis of macromolecular dynamics.

Given that the OPs evolve much slower than the $10^{-14}$ second timescale of atomistic collisions/vibrations, the latter have sufficient time to arrive at a quasi-equilibrium consistent with the instantaneous state of the OPs. The OPs modify the probability distribution of atomistic configurations which, in turn, determine the thermal-average forces and diffusivities mediating OP dynamics. In this view, macromolecular structural dynamics follows from the coupling of processes across multiple scales in space and time. The result of the multiscale analysis of the Newtonian Liouville equation is a set of Langevin equations of stochastic OP dynamics. If the set of OPs is incomplete (i.e., its dynamics is coupled to that of other slowly changing variables), then the OPs satisfy equations involving time delays (i.e., memory effects), as results from traditional projection operator analysis. In contrast, the multiscale analysis presented here does not involve these memory effects because of the timescale separation enabled by the OPs.

According to the present disclosure, the introduction of OPs serves several objectives: (1) providing a set of OPs for macromolecules that capture the essence of macromolecular structural dynamics, (2) providing an efficient computational algorithm to simulate structural dynamics, and (3) demonstrating the applicability of the OPs to a multiscale algorithm via viral RNA simulations. Each of these will be discussed, in turn, below. It is desirable that the construction of macromolecular OPs be automatable, so that: (1) the description can readily be enriched if it is found to be incomplete, and (2) the tedious process of inventing new OPs for each macromolecule is avoided. The OPs should also capture key features of the free-energy landscape in order to be complete dynamically. In this way, the OPs may capture key pathways for structural transitions and associated energy barriers.

As disclosed herein, a multiscale analysis of a macromolecule involves the identification of OPs that describe the macromolecule's nano-scale features. One property of an OP is that it evolves slowly. Slow OP dynamics emerge in several ways including inertia associated with the coherent dynamics of many atoms evolving simultaneously, migration over long distances, stochastic forces that tend to cancel, and species population levels as in chemical kinetics or self-assembly which involve many units, only a few of which change on the atomic timescale.

The presently disclosed OPs relate macromolecular features to a reference structure (e.g., from X-ray crystallography). The OPs are introduced via (1) a transformation warping space and (2) maximizing their information content to relate them to the atomistic configurations. OPs may be constructed by embedding the system in a volume $V_S$. Basis functions $U_{\underline{k}}(\bar{r})$ for a triplet of labeling indices $\underline{k}$ may be introduced. If computations are carried out using periodic boundary conditions to simulate a large system (e.g., to minimize boundary effects and to handle Coulomb forces), periodic basis functions (Fourier modes) may be used. In other embodiments, the basis functions may be spherical harmonics when the system is embedded in a spherical volume. More generally, the basis functions used may be chosen for convenience to reflect the overall geometry of the system and the conditions imposed at the boundary. Furthermore, the basis functions may be free of unphysical features (e.g., poles). In one illustrative embodiment, Legendre polynomials were found to be convenient for simulating systems with closed boundaries of rectangular geometry.

In the present disclosure, points $\bar{r}$ within the system are considered to be a displacement of original points $\bar{r}^o$. A set of vector OPs $\bar{\Phi}_{\underline{k}}$ may be constructed as follows. The macromolecule deforms in 3-D space such that a point $\bar{r}$ is displaced from an original point $\bar{r}^o$. Deformation of space taking any $\bar{r}^o$ to $\bar{r}$ is continuous and is used to introduce OPs $\bar{\Phi}_{\underline{k}}$ via $$\bar{r} = \sum_{\underline{k}} U_{\underline{k}}(\bar{r}^o) \bar{\Phi}_{\underline{k}}. \tag{1}$$

As the $\bar{\Phi}_{\underline{k}}$ change, space is deformed, and so is the macromolecule embedded in it. The objective is to ensure that the dynamics of the $\bar{\Phi}_{\underline{k}}$ reflects the physics of the macromolecule and that the deformation captures key aspects of the atomic-scale details of the structure. In this way, the $\bar{\Phi}_{\underline{k}}$ constitutes a set of vector OPs if they are slowly varying in time.

The $i^{th}$ atom in the macromolecule (i=1, . . . N) may be moved from its original position $\vec{r}_i^o$ via the above deformation by evolving the $\underline{\Phi}_k$ and correcting for atomic-scale details as follows. Given a finite truncation of the $\underline{k}$ sum in Eq. (1), for example, choosing $N_{OP}$ number of OPs, there will be some residual displacement (denoted $\vec{\sigma}_i$) for each atom in addition to the coherent deformation generated by the $\underline{k}$ sum:

$$\vec{r}_i = \sum_{\underline{k}} \underline{\Phi}_k U_{\underline{k}}(\vec{r}_i^o) + \vec{\sigma}_i. \quad (2)$$

To maximize the information content of the OPs, the magnitude of the $\vec{\sigma}_i$ can be minimized by the choice of basis functions and the number of terms in the $\underline{k}$ sum. Conversely, imposing a permissible size threshold for the residuals allows one to determine the number of terms to include in the $\underline{k}$ sum.

To start the multiscale analysis, the $\underline{\Phi}_k$ should be expressed in terms of the fundamental variables $\vec{r}_i$. To arrive at this relationship, the mass-weighted square residual $(m_1\sigma_1^2 + \ldots m_N\sigma_N^2)$ is minimized with respect to the $\underline{\Phi}_k$, where $m_i$ is the mass of atom i. This implies $$\sum_{\underline{k}'} B_{\underline{k}\underline{k}'} \underline{\Phi}_{k'} = \sum_{i=1}^{N} m_i U_{\underline{k}}(\vec{r}_i^o) \vec{r}_i, \, B_{\underline{k}\underline{k}'} = \sum_{i=1}^{N} m_i U_{\underline{k}}(\vec{r}_i^o) U_{\underline{k}'}(\vec{r}_i^o). \quad (3)$$

Thus, the OPs can be computed in terms of the atomic positions by solving Eq. (3). For convenience, the basis functions $U_{\underline{k}}$ may be mass weighted orthogonal. In that case, the B-matrix of Eq. (3) is diagonal. $U_{\underline{k}}(\vec{r}_i^o)$ is viewed in this embodiment as the $i^{th}$ component of an N-dimensional vector for an N-atom macromolecule. There are $N_{OP}$ N-dimensional vectors, each labeled by its $\underline{k}$ value. Orthogonalization of these vectors may be carried out using a Gram-Schmidt procedure. In the above notation, $\underline{k}$ is a set of integers (each of which can be 0, 1, . . . ); with this, $\Phi_{100X}$ is the X component of the OP $\underline{\Phi}_{100}$ that weights the $U_{100}$ contribution in Eq. (2) after the latter has been subjected to Gram-Schmidt orthogonalization. In this illustrative embodiment, before orthogonalization, $U_{k_1 k_2 k_3}$ is a product of Legendre polynomials of order $k_1$, $k_2$, $k_3$ for the X, Y, Z components of $\vec{r}_i^o$ respectively. The orthogonalization scheme preserves the physical nature of the three fundamental OPs (100X, 010Y, 001Z) because they are chosen to be the first three members of the basis. For other OPs, the $\underline{k}$ labeling corresponds to the original $U_{\underline{k}}(\vec{r}_i^o)$ from which each orthogonal vector was constructed via the Gram-Schmidt procedure.

Mass-weighted orthonormality of the basis functions implies that $B_{\underline{k}\underline{k}'}$ is 0 for $k \neq k'$. As such, $$\underline{\Phi}_k = \frac{\sum_{i=1}^{N} m_i U_{\underline{k}}(\vec{r}_i^o) \vec{r}_i}{\tilde{\mu}_k}, \, \tilde{\mu}_k = \sum_{i=1}^{N} m_i \{U_{\underline{k}}(\vec{r}_i^o)\}^2. \quad (4)$$

Thus, for a given set of atomic positions the corresponding OPs are uniquely defined.

In considering the timescale of OP dynamics, the Liouville operator may be defined as $$L = -\sum_{i=1}^{N} \frac{\vec{p}_i}{m_i} \cdot \frac{\partial}{\partial \vec{r}_i} + \vec{F}_i \cdot \frac{\partial}{\partial \vec{p}_i},$$

where $\vec{p}_i$ and $\vec{F}_i$ are the momentum of, and the net force on, atom i. Given Eq. (4), one may compute $$\frac{d\Phi}{dt} \text{ as } -L\Phi,$$

where $\underline{\Phi}(\Gamma)$ is a set of OPs $\underline{\Phi}_k$.

$$\frac{d\underline{\Phi}_k}{dt} = \frac{\vec{\Pi}_k}{\tilde{\mu}_k}, \quad (5)$$

$$\vec{\Pi}_k = \sum_{i=1}^{N} U_{\underline{k}}(\vec{r}_i^o) \vec{p}_i.$$

Inclusion of $m_i$ in developing Eq. (3) gives $\underline{\Phi}_k$ the character of a generalized center-of-mass-like (CM) variable. In fact, if $U_{\underline{k}}$ is a constant then $\underline{\Phi}_k$ is proportional to the CM. While the $\underline{\Phi}_k$ are given in terms of a sum of N-atomic displacements, many terms of which have similar directions due to the smooth variation of $U_{\underline{k}}$ with respect to $\vec{r}_i^o$, the momenta $\vec{\Pi}_k$ are given by a sum of atomic momenta, which tend to cancel near equilibrium. Hence, the thermal average of $\vec{\Pi}_k$ is small, and thus the $\underline{\Phi}_k$ tend to evolve slowly.

Considering the dynamics of the CM variable, from Eq. (5), $\underline{\Phi}_{000}$ satisfies $$\frac{d\underline{\Phi}_{000}}{dt} = \frac{\vec{\Pi}_{000}}{M},$$

where $\tilde{\mu}_{000} = M$ is the total mass of the macromolecule. Since M is large, $\underline{\Phi}_{000}$ evolves slowly relative to the timescale of atomic collision/vibration. This suggests that $\underline{\Phi}_{000}$ satisfies a key criterion to be an OP and serves as the starting point of a multiscale analysis.

To reveal the timescale on which the OPs evolve, it is convenient to define the smallness parameter $\epsilon = m/M$, where m is a typical atomic mass. For any of the $\underline{\Phi}_k$, letting $\vec{v}_i$ be the velocity of particle i, the definition of $\epsilon$ and Eq. (5) yields $$\frac{d\underline{\Phi}_k}{dt} = \frac{\sum_{i=1}^{N} U_{\underline{k}}(\vec{r}_i^o) \vec{p}_i}{\tilde{\mu}_k} = \quad (6)$$

$$\frac{\sum_{i=1}^{N} U_{\underline{k}}(\vec{r}_i^o) m_i \vec{v}_i}{\tilde{\mu}_k} = \frac{\sum_{i=1}^{N} U_{\underline{k}}(\vec{r}_i^o) m \hat{m}_i \vec{p}_i}{M \tilde{\mu}_k} = \frac{\sum_{i=1}^{N} U_{\underline{k}}(\vec{r}_i^o) \hat{m}_i \vec{v}_i}{\tilde{\mu}_k} = \epsilon \frac{\vec{\Pi}_k}{\tilde{\mu}_k},$$

where $\mu_k = \tilde{\mu}_k / M$ and $\hat{m}_i = m_i/m$.

Thus, $\underline{\Phi}_k$ changes at a rate $O(\epsilon)$ under the assumption that the atomic momenta tend to cancel, as is consistent with the quasi-equilibrium probability distribution $\hat{\rho}$ below. Special initial conditions could make the rate of OP change scale differently. Illustrative examples of such conditions include an initial density discontinuity (leading to a shockwave), injection of the macromolecule at a high velocity, or a sudden jump in temperature. Under these conditions the slowness of motion within our reduced dimensionality framework (OPs) and all the resulting advantages (e.g., calculating thermal-average forces) may be lost. Therefore, for any class of initial conditions, the slow rate of OP dynamics may be confirmed before applying the multiscale ideas developed below. The present disclosure demonstrates the applicability of the ϵ-scaling for typical conditions underlying macromolecular behavior.

A simple case of the $\bar{r}_i, \bar{\Phi}_k$ relationship suggests how it captures rigid rotation. Take $\underline{U}_k, k=100, 010, 001$ to be $x^o, y^o,$ and $z^o$ respectively. Neglecting the residuals, Eq. (2) becomes $x_i = \Phi_{100x}x_i^o + \Phi_{010x}y_i^o + \Phi_{001x}z_i^o$, and similar for $y_i$ and $z_i$ (where $x_i, y_i, z_i$ are the three Cartesian components of $\bar{r}_i$ vector). The relationship can be written in the tensorial form $\bar{r}_i = \overline{\overline{\Phi}} \bar{r}_i^o$. For a special case (i.e., where the tensor $\overline{\overline{\Phi}}$ is a rotation matrix), $\bar{\Phi}_k$ constitutes a length preserving rotation about the CM if $\bar{r}_i$ is relative to the CM. More generally, for the above three basis functions, the $\bar{r}_i - \bar{\Phi}_k$ relationship corresponds to a mixed rotation, extension/compression. The OPs defined here constitute a strain tensor thereby accounting for elastic deformations. In addition, the presently disclosed multiscale formulation is all-atom and, hence, captures internal friction effects via the force-field. This accounts for both elastic and viscous effects. The higher order OPs (specifically second and third order) capture twisting, bending, and more complex deformations. Such OPs may capture polyalanine folding from a linear to a globular state. The OPs may also capture nucleation and front propagation in a virus capsid. While it is not trivial to interpret all the deformations associated with the higher order polynomial-defined OPs, it is the generality of the presently disclosed multiscale approach that accounts for all their dynamics. Ultimately the interpretation of the OPs is embodied in the description of the phenomenon itself, e.g., macromolecular structural transition.

The relationship between $\bar{\Phi}_k$ and $\bar{r}_i$ is taken here to be linear. This ensures that r has a unique value for a given set of $\bar{\Phi}_k$ and residuals (Eq. (2)). Should this not be the case, as Newton's equations evolve $\underline{r}$, the system could spontaneously transition to another state of order without a change of microstate. By similar arguments, application of $$\sum_{\underline{k}'} B_{\underline{k}\underline{k}'} \bar{\Phi}_{\underline{k}'} = \sum_{i=1}^{N} m_i U_{\underline{k}}(\vec{r}_i^o) \bar{g}(\vec{r}_i),$$

where $\bar{g}$ is a function of $\underline{r}_i$, may not always be suitable. This would have been implied by replacing Eq. (2) with $$\bar{g}(\vec{r}_i) = \sum_{\underline{k}} \bar{\Phi}_{\underline{k}} U_{\underline{k}}(\vec{r}_i^o) + \bar{\sigma}_i.$$

If $\bar{g}$ is linear in $\bar{r}_i$, then the unique relation between $\bar{\Phi}_k$, residuals, and $\bar{r}_i$ holds, allowing for the multiscale analysis presented above. However, if $\bar{g}$ is a nonlinear function of $\bar{r}_i$ then this uniqueness may be lost; multiple solutions for $\bar{r}_i$ could exist for a given set of $\bar{\Phi}_k$ and residuals. This could create situations wherein an initial $\underline{r}$ state evolves to multiple states allowed by the nonlinearity of $\bar{g}$. Newtonian mechanics prohibits this dynamical bifurcation of states (i.e., simultaneous evolution of one state into multiple ones). Hence, in the present OP construction, inclusion of a nonlinear function $\bar{g}$ could lead to unphysical results if uniqueness of the $\underline{r}-\underline{\Phi}$ relationship is violated. In other embodiments, other transformations may be designed that allow for nonlinear combinations of $\underline{r}$ without violating this uniqueness. The suggested bifurcation of states should not be confused with the multiplicity of atomic configurations that arise due to $\bar{\sigma}_i$ sampling, as described above. The illustrative embodiment does not imply that the OP dynamics are linear, i.e., the thermal-average forces driving OP dynamics in general are related to the OPs in a highly nonlinear fashion. This nonlinearity is important in simulating far-from equilibrium structures.

In the above context, Eq. (4) is the origin of the unique value of $\bar{\Phi}_k$ for a given set of $\bar{r}_i$. While $\underline{r}$ implies $\bar{\Phi}_k$ uniquely, the converse is not true, i.e., there is an ensemble of $\underline{r}$ for given $\underline{\Phi}$. This stems from the fact that a theory with $N_{OP}(<<N)$ OPs cannot predict 3N atomic co-ordinates uniquely; this is the motivation for adding the residuals to Eq. (1) and generating an ensemble of atomic configurations consistent with the OPs (Eq. (2)). In particular, $N\bar{r}_i$ cannot be uniquely expressed in terms of $N_{OP}\bar{\Phi}_k$ from Eq. (3) or Eq. (4). Therefore, the $\underline{r}-\underline{\Phi}$ relationship is not one-to-one.

The set $\underline{\Phi}$ of OPs have technical advantages that greatly facilitate theoretical analyses. Consider an extended set $\underline{\Phi}_{ex}$ of OP and OP-like variables, notably the $\bar{\Phi}_k$ for $\underline{k}$ in the list of OPs plus similarly defined variables $\bar{\Phi}_{k_{res}}$ for $\underline{k}$ not in the OP list. Thus, $$\vec{r}_i = \sum_{\underline{k}}{}^{OP}\bar{\Phi}_{\underline{k}} U_{\underline{k}}(\vec{r}_i^o) + \sum_{\underline{k}}{}^{res}\bar{\Phi}_{\underline{k}_{res}} U_{\underline{k}}(\vec{r}_i^o) \qquad (7)$$

This relation maps the 3N configuration variables $\underline{r}$ onto $\underline{\Phi}_{ex}$, also a 3N-dimensional space. Eq. (7) for $\bar{r}_i$ in terms of $\underline{\Phi}$ and $\underline{\Phi}_{res}$ provides a way to generate ensembles of $\bar{\Phi}_k$-constrained configurations by randomly varying the $\bar{\Phi}_{k_{res}}$. An expression for $\bar{\sigma}_i$ in terms of $\underline{\Phi}_{res}$ may be obtained by comparing Eq. (2) and Eq. (7). However, generating ensembles by randomly varying the $\bar{\sigma}_i$ typically leads to very high-energy configurations. This difficulty may be avoided as long as $\bar{\sigma}_i$ is chosen by constraining $\bar{\Phi}_{k_{res}}$ for higher order $\underline{k}$ to small values. The lower $\underline{k}-\bar{\Phi}_{k_{res}}$ do provide major structural variations by moving atoms in the ensemble with a measure of coherence, avoiding near-atom overlap. Thus, $\bar{\Phi}_{k_{res}}$ provides a way to generate rich ensembles at fixed $\underline{\Phi}$ and with modest energies (and, hence, Boltzmann relevance). In practice a "hybrid" sampling method, wherein short MD runs are performed starting with configurations from the $\bar{\Phi}_{k_{res}}$-generated sample, may be used to enrich fluctuations about the constant set of OPs $\underline{\Phi}$. All these properties are important for the practical implementation of a multiscale approach in the DMS.

It should be noted that, even though the OPs are defined in terms of atoms in the macromolecule, the multiscale analysis described herein accounts for both the macromolecule and the medium, allowing simulation of the entire system. Since the OPs evolve on a long timescale, their dynamics filter out the high frequency atomistic fluctuations (residuals). The slowly evolving OPs can be projected over large intervals in time. These timesteps are appreciably larger than simple MD timesteps and, therefore, efficiently probe the long time behavior of a macromolecule. As the OPs are generated in an automated fashion, the set may be expanded by increasing the range of the $\underline{k}$ sum. As further discussed below, this addresses the difficulty that arises when a limited set of OPs couples to other slow variables.

The OPs discussed above and the Liouville equation may be used to derive equations for the stochastic dynamics of a macromolecule. The analysis starts by writing the Liouville equation for the N-atom probability density $\gamma$, i.e., $\partial \gamma/\partial t = L\gamma$ for Liouville operator $L$. $\gamma$ depends on the set of 6N positions, momenta $\Gamma$, and time t.

The multiscale analysis starts with a transformation of the N-atom probability density from the $\gamma(\Gamma,t)$ formulation to one that makes the multiple ways on which $\gamma$ depends on $\Gamma$,t more explicit. This involves introduction of a set of OPs $\underline{\Phi}(\Gamma)$ (i.e., $\Phi_{\underline{k}}$, as described above, for all $\underline{k}$ on the list of OPs) that depends on $\Gamma$ and that are shown to evolve on a timescale much greater than that of individual atomic collisions/vibrations.

First, $\gamma$ may be written in a form that makes the dependence on $\Gamma$ and t of various types explicit:

$$\gamma(\Gamma,t) = \rho\{\Gamma_0(\Gamma), \underline{\Phi}(\Gamma), t_0(t), \underline{t}(t); \epsilon\} \quad (8)$$

This makes an ansatz that reformulated probability density $\rho$ depends on the N-atom state $\Gamma$ both directly (i.e., via $\Gamma_0(\Gamma)=\Gamma$) and, via a set of OPs $\underline{\Phi}(\Gamma)$, indirectly. Similarly, $\rho$ depends on the sequence of times $t_0(t), t_1(t), t_2(t), \ldots = t_0(t), \underline{t}(t)$, where $t_n(t) = \epsilon^n t$. The times $t_n$ for $n>0$ are introduced to account for the slower behaviors in $\rho$, while $t_0$ accounts for processes on the fast timescale (i.e., $t_0$ changes by one unit when $10^{-14}$ seconds elapse). $\epsilon$ is a small parameter, as defined above. The $\epsilon$ dependence of $\rho$ and scaling of time are justified below.

In adopting this perspective, $\underline{\Phi}$ is not a set of additional independent dynamical variables; rather, its appearance in $\rho$ is a place-holder for a special dependence of $\rho$ on $\Gamma$ that underlies the slow temporal dynamics of $\rho$. A simple example that elucidates the ansatz is the function $f(x) = \exp^{-\epsilon x} \sin(x)$. $f(x)$ may be restated as $f(x_0, x_1)$, where $x_0 = x$ and $x_1 = \epsilon x$. This transformation does not add any independent variable to the description; rather, it makes the discrete dependencies on x explicit. It is shown below that the dual dependence of $\rho$ on $\Gamma$ can be constructed if $\epsilon$ is sufficiently small. An equation of stochastic OP dynamics that preserves the feedback between the atomistic and nano-scale variables is now obtained via a multiscale perturbation analysis for a classical N-atom system.

The above framework may be used to derive an equation for the OP probability distribution. One finds that $L\Phi$ naturally reveals a small parameters (as described above). Starting with Eq. (8), the Liouville equation for $\gamma$, and the chain rule, one obtains the multiscale Liouville equation:

$$\sum_{n=0}^{\infty} \varepsilon^n \frac{\partial \rho}{\partial t_n} = (L_0 + \varepsilon L_1)\rho. \quad (9)$$

Eq. (9) may be solved perturbatively via a Taylor expansion in $\epsilon$. $L_0$ involves partial derivatives with respect to $\Gamma_0$ at constant $\underline{\Phi}$ (when operating on $\rho$ in the multiscale form, Eq. (8)), and conversely for $L_1$. As such, $L_0$ and $L_1$ take the forms:

$$L_0 = -\sum_{i=1}^{N} \frac{\vec{p}_i}{m_i} \cdot \frac{\partial}{\partial \vec{r}_i} + \vec{F}_i \cdot \frac{\partial}{\partial \vec{p}_i}, \quad (10)$$

$$L_1 = -\sum_{\underline{k}} \frac{\Pi}{\mu_{\underline{k}}} \cdot \frac{\partial}{\partial \underline{\Phi}}. \quad (11)$$

Note that $L_0$ and $L_1$ operate in the space of functions that depend explicitly on variables $\Gamma_0$ and $\underline{\Phi}$; $\underline{\Pi}$ signifies a set of $\Pi_{\underline{k}}$ and subscripts 0 on $\vec{r}_i$ and $\vec{p}_i$ in Eq. (10) are henceforth dropped because of the simple $\Gamma_0(\Gamma)=\Gamma$ dependence of $\rho$. While the space of functions on which $L_0$ and $L_1$ operates is composed of $6N+N_{OP}$ variables (the 6N atomic positions and momenta $\Gamma_0$, plus the $N_{OP}$ OPs $\underline{\Phi}$), this does not assume that the variables are dynamically independent. Rather, from Eq. (9), the dependence of $\rho$ on $\Gamma_0$ and $\underline{\Phi}$ may be determined, and ultimately, through Eq. (8), how $\gamma$ depends on $\Gamma$. Hence, Eqs. (9)-(11) do not imply that $\Gamma_0$ and $\underline{\Phi}$ are independent dynamic variables but, in accordance with Eq. (8), the equations track the multiple space and time dependencies of $\gamma$. There are still 6N dynamical variables, as the OPs do not evolve independently of the 6N atomic positions and momenta. Eq. (4) and Eq. (6) show the explicit dependencies of atomic and coarse-grained quantities. In summary, to uncloak the explicit space-time dependencies of the N-particle density $\gamma$, $6N+N_{OP}$ variables are used, of which $N_{OP}$ are not independent of the remainder (with dependencies defined via Eq. (4) and Eq. (6)). As no additional independent variables are added to the description of the N-atom system, $\gamma$ still remains a function of the 6N dynamical variables. Furthermore, the $O(\epsilon)$ scaling of the Liouville equation is a natural consequence of the slowness of OPs. This justifies a perturbative solution and hence the $\epsilon$ dependence of the N-atom probability density. With this, the N-atom probability density may be constructed as $$\rho = \sum_{n=0}^{\infty} \varepsilon^n \rho_n.$$

Putting the perturbation expansion for $\rho$ into Eq. (9), and analyzing different orders in $\epsilon$, the Smoluchowski equation for the coarse-grained probability distribution $\tilde{W}$ is obtained:

$$\frac{\partial \tilde{W}}{\partial \tau} = \sum_{\underline{kk'}} \frac{\partial}{\partial \Phi_{\underline{k}}} \left[ \vec{D}_{\underline{kk'}} \left[ \frac{\partial}{\partial \Phi_{\underline{k'}}} - \beta \vec{f}_{\underline{k'}} \right] \tilde{W} \right]. \quad (12)$$

The diffusivity factors $\vec{D}_{\underline{kk'}}$ are related to the correlation function of time derivatives of OPs via:

$$\vec{D}_{\underline{kk'}} = \frac{1}{\mu_{\underline{k}} \mu_{\underline{k'}}} \int_{-\infty}^{0} dt'_0 \langle \Pi_{\underline{k}} e^{-L_0 t'_0} \Pi_{\underline{k'}} \rangle, \quad (13)$$

where $\Pi_{\underline{k}}$ is defined in terms of the OP time derivatives via Eq. (5) and Eq. (6). In constructing the correlation functions, the initial data is at fixed $\underline{\Phi}$. Since $\underline{\Phi}$ does not change appreciably during the period in which the correlation function is appreciable, $\vec{D}_{\underline{kk'}}$ depends on $\underline{\Phi}$. The thermal-average force $\vec{f}_{\underline{k}}$ given by:

$$\vec{f}_k = -\frac{\partial F}{\partial \underline{\Phi}_k} = \langle \vec{f}_k^{m*} \rangle \quad (14)$$

for $\underline{\Phi}$ constrained Helmholtz free-energy F, where $$F = -\frac{1}{\beta}\ln Q(\underline{\Phi}, \beta), \quad (15)$$

$Q(\underline{\Phi},\beta)$ is the partition function associated with $\hat{\rho}$, and $$\vec{f}_k^{m*} = \sum_{i=1}^N U_k(\vec{r}_i^{\,o})\vec{F}_i^{\,*}$$

is the "OP force."

Equivalent to Eq. (12) is an ensemble of OP time courses generated by the Langevin equations:

$$\frac{\partial \underline{\Phi}_k}{\partial \tau} = \beta \sum_{k'}\left[\overleftrightarrow{D}_{kk'}\vec{f}_{k'}\right] + \vec{\xi}_k \quad (16)$$

The coherent part of the evolution is determined by the product of the diffusivities and the thermal-average forces; the stochastic evolution is determined by the random force $\vec{\xi}_k$. The diffusivities may be constrained by requiring the integral of their auto-correlation function to be proportional to the diffusion coefficient.

The expression for diffusivities provided above involves an integration of the correlation function over all time. However, if the correlation function decays on a long timescale (i.e., on that comparable to OP evolution), the above Smoluchowski equation would be replaced by one that is non-local in time. This would suggest that the set of OPs couples to other slow variables. Since the OPs are generated automatically (as described above), new slow variables can be added in a straightforward way to make the existing set $\underline{\Phi}$ complete (e.g., eliminating the long-time tail). Completing the set of OPs modifies the operator $L_0$ (and hence the velocity correlation of Eq. (13)), as the latter involves derivatives with respect to $\Gamma_0$ at constant $\underline{\Phi}$. This modifies the diffusivities, affecting dynamics of the OPs on the free-energy surface they define. Such an operator is automatically accounted for via standard MD codes when the correlation time of OP velocities is short relative to the timescale of OP evolution. Thus, the long-time behavior of correlation functions provides a completeness criterion for the set of OPs and, thereby, a self-consistency check for the theory and computations.

Another self-consistency check is related to refreshing of the reference structure $\underline{r}^o$. In the illustrative embodiment, simulations begin with the energy-minimized and thermally equilibrated X-ray crystallographic or other all-atom structure as the reference structure. As the system evolves in time, the resulting deformation may increase some of the residuals. This may reflect the need for a new reference structure. The reference structure transition point is chosen when the maximum residual for a structure in the constant OP ensemble becomes comparable with its root mean square deviation (RMSD) from the initial reference structure $$\left[\frac{|\vec{r}_1 - \vec{r}_1^o|^2 + \ldots |\vec{r}_N - \vec{r}_N^o|^2}{N}\right]^{1/2}$$

(i.e., when some local change in a structure reaches the order of an overall deformation). The increase in residual may indicate the presence of coherent motions that are not accounted for by the set of OPs initially chosen. If the emerging modes couple to the previously defined set of OPs, long-time OP velocity auto-correlation tails are also expected. The remedy for this situation is to increase the number of OPs considered, a process greatly facilitated by the automatic generation of OPs. Increase in the residuals may indicate the presence of an improbable fluctuation in the MD generated part of the finite ensemble used for a practical computation. This increase is generally minimized via the low $\underline{k}$-$\Phi_{kres}$ sampling and, for the thermal-average forces, via the Boltzmann factor (structures with larger values of $\Phi_{kres}$ for higher order $\underline{k}$ tend to be high in energy). However, for these cases, a simple reference structure renewal would suffice to account for the resulting motions, and additional OPs are not required.

As discussed above, new OPs may be added in order to redefine the set of OPs (e.g., to eliminate the long-time tails of correlation functions) and to account for the systematic growth of residuals that is not accounted for via re-referencing. In principle, a simple addition of higher order OPs to the set of existing ones until the complete elimination of the long-time correlation tail would suffice. However, this might include some unnecessarily high frequency modes as OPs. As a result, the Langevin timestep would be reduced, affecting the efficiency of multiscale simulation. Efficiency may be restored by optimal choice of the OPs to be added. For example, a nanosecond MD run may be performed, and the resulting configuration time courses may be used to rank the omitted OPs according to their average rate of change. Variables that qualify as OPs are slow and coherent, whereas residuals (that are described by $\Phi_{kres}$) are highly fluctuating with mean close to zero (further discussed below). The former may be added, one at a time, to the list of existing OPs, and new ensembles may be generated by sampling the remaining variables. This process may be repeated till the residuals become reasonably small and the long-time tail in the auto-correlation function is eliminated. This procedure favors the addition of slow variables and, hence, consideration of high frequency modes as OPs may be avoided. Such a procedure may also be used in selecting OPs to start the simulations.

Multiscale analysis provides a numerical simulation approach implied by the feedback between nano and atomic scale variables. As $\vec{f}_k$ and $\overleftrightarrow{D}_{kk'}$ are OP-dependent, they are computed at each Langevin timestep to account for the inter-scale feedback. A finite Langevin timestep $\Delta t$ advancement takes the OPs from time t to a time t+$\Delta t$ via Eq. (16). Thermal forces $\vec{f}_k$ may be efficiently computed via an ensemble/Monte Carlo integration method enabled by the nature of the OPs. Atomic forces obtained from the residual generated OP constrained ensemble are used to calculate the OP force $\vec{f}_k^{\,m}$. Monte Carlo integration averaging of $\vec{f}_k^{\,m}$ over the ensemble is carried out to obtain the thermal ($\hat{\rho}$) average force $\vec{f}_k$. Hence, the free-energy driving force is obtained via the all-atom probability density $\hat{\rho}(\Gamma_0,\underline{\Phi})$, capturing the cross-talk between the OPs and individual atomic degrees of freedom. Since $\hat{\rho}(\Gamma_0,\underline{\Phi})$ reflects the OP constrained ensemble, the 6N atomic degrees are consistent with the state of the OPs. It should be noted that the definition of $\vec{f}$ $k$ as OP derivative of free-energy in Eq. (14), and $\overline{D}_{kk'}$ as time integral of OP velocity auto-correlation function in Eq. (13) is independent of the linearity in the $r$–$\Phi$ relationship. This implies that the multiscale analysis developed can be applied to any complete set of slow variables provided that the $O(\epsilon)$ time scaling and Newton's laws of motion hold for their dynamics. The presently disclosed OPs form a set of slow variables that has suitable properties to serve as a basis for a deductive multiscale simulation. It will be appreciated that other sets of slow variables can also be used, in other embodiments, as long as the criteria for OPs dynamics are satisfied.

The diffusivities may be computed via the correlation functions of Eq. (13) using short MD runs, because the correlation times in these functions are much shorter than the characteristic timescale of OP evolution. All factors in the OP dynamics equation, Eq. (16), are computed from the inter-atomic force-field via Monte Carlo integration and MD. Thus, the only element of calibration in constructing the thermal-average forces and diffusivities is through the existing force-fields (e.g., CHARMM or AMBER). At each Langevin timestep, the updated OPs are used to generate the atomistic configurations of the macromolecule; then, the host medium is introduced via a re-solvation module and the entire system is thermalized. An ensemble of such equilibrated atomistic configurations is used to generate the thermal-average forces and diffusivities. The latter factors are used to evolve the OPs via Langevin dynamics, completing one cycle of the Langevin timestepping.

This method 100 of interscale feedback from the OPs 102 to the ensemble of atomistic configurations 104 (characterized by the quasi-equilibrium probabilities) and, in turn, back to the OPs 102, is summarized as a simplified flow diagram in FIG. 1. The method 100 may begin with a reference structure that is cast in terms of variables describing the systems at the shortest space-time scale. In the illustrative embodiment, this fine-scale description is cast in terms of the positions and momenta of all atoms in the system. As described above, the method 100 may construct a set of OPs 102 that model the structural characteristics of the system, e.g., the position, shape, size, and orientation of major components of a macromolecule. As shown in FIG. 1, as the OPs 102 evolve slowly in time, the OPs 102 change the conditions determining the ensemble of atomistic configurations 104. In the illustrative embodiment, the ensemble atomistic configurations 104 are described by an equilibrium distribution following from entropy maximization constrained to instantaneous values of the OPs 102. The method 100 may next involve determining thermal-average forces and diffusivities 106 arising from the molecular dynamics of the ensemble atomistic configurations 104. In the illustrative embodiment, the thermal-average forces and diffusivities 106 are efficiently computed using an ensemble/Monte Carlo integration method. Finally, these thermal-average forces and diffusivities 106 drive the Langevin dynamics of the OPs 102, completing a feedback loop in the method 100. In one illustrative embodiment, the method 100 may be performed iteratively over a plurality of Langevin timesteps by the DMS.

In the illustrative embodiment describe above, the OPs are defined over the macromolecule. As with the atomic configurations of the macromolecule, water and ions are accounted for via the quasi-equilibrium ensemble (i.e., the configuration of the water and ions rapidly explores a quasi-equilibrium ensemble at each stage of the OP dynamics). This assumption holds only when water and ions equilibrate on a timescale much smaller than that of OPs. Fluctuations from water and ions modulate the residuals generated within the MD part of the constant OP sampling and affect the thermal-average force. As such, the water and ions may be excluded from the definition of the OPs (as discussed above). If slow hydrodynamic modes are found to be of interest, however, these atoms may be included in the definition of the OPs. Ions tightly bound to the macromolecule may be considered a part of OPs. After every Langevin timestep, an ion accessible surface is constructed, and ions close to the surface are tracked during the MD ensemble enrichment calculation. Ions with appreciable residence time within the surface are included in the definition of the OPs henceforth.

As mentioned above, for some choice of initial data, the $O(\epsilon)$ contribution to $\tilde{W}(\Phi,t)$ can have short timescale dependence (e.g., due to a shock wave). Under this condition, the basic assumption of the lowest order quasi-equilibrium behavior is violated, as the $O(\epsilon)$ scaling of the OP motion is disturbed. In such a case, one expects Fokker-Planck behavior. The present formulation may be generalized to accommodate such inertial effects. For the illustrative macromolecular phenomena considered below, however, this class of initial data was ignored.

A study was undertaken to assess performance of the OPs described above in a DMS for simulating macromolecules. An evaluation of other variables in this context was also obtained. Comparisons with traditional MD were made to determine accuracy and efficiency. All multiscale simulations were done using the DMS based on the OPs and the multiscale analysis described above. In the illustrative embodiment, the CHARMM22/27 force-field and NAMD software were incorporated into the DMS as part of the computation of the thermal-average forces and diffusivities.

The demonstration system was the RNA of a Satellite Tobacco Mosaic Virus (STMV). This molecule contains 949 nucleotides. The initial state of this system is believed to be at equilibrium when the RNA resided with the associated proteins within the STMV capsid. Evolution follows instantaneously after the capsid is removed. The simulated host medium was 0.3M NaCl solution and the temperature was 300K. The system was placed within a cube and NVT conditions were applied. Details of the NAMD settings are given in Table 1 below. Simulations were done in these conditions, as more dramatic structural changes occur because the RNA is more stabilized by $Mg^{2+}$ than by $Na^+$. This is because $Na^+$ is expected to be diffusively bound to RNA, whereas $Mg^{2+}$ remain tightly bound.

TABLE 1

| PARAMETER | VALUE(S) |
| --- | --- |
| Temperature | 300 K |
| Langevin damping | 5 |
| Timestep | 1 fs |
| fullElectFrequency | 2 fs |
| nonbondedFreq | 1 fs |
| Box size | 145 Å × 145 Å × 145 Å* or 162 Å × 162 Å × 162 Å** |
| Force-field parameter | par_all27_prot_na.prm |
| 1-4scaling | 1.0 |
| Switchdist | 10.0 Å |
| Cutoff | 12.0 Å |
| Pairlistdist | 20.0 Å |
| Stepspercycle | 2 |
| Rigid bond | Water |

*Box for free RNA simulation for 3 ns.
**Box for free RNA simulation from 3 ns-50 ns and protein-bound RNA.

As mentioned above, the slowness in rate of change of a typical OP (001Z) was examined to evaluate its applicability within the multiscale framework. The OP considered, in particular, exhibited properties of dilation/extension about the Z-axis. The time evolution of this OP was compared to other variables to validate that some of the latter are not suitable as slow variables for the purpose of a multiscale analysis. If the fluctuations in these variables probe short space-time events, then they are expected to be accounted for by the quasi-equilibrium ensemble; otherwise, larger space-time events are accounted for by one or more of the OPs.

Some other variables commonly used to characterize macromolecules, denoted "structural parameters" (SPs) herein, may be compared with the dynamics of the OPs described above. The SPs analyzed in the present disclosure are different types of dihedrals and their cosines, radius of gyration, end-to-end distances, and typical components of the unit vectors along the bonds connecting monomers. These SPs are designated herein as $SP_1$, $SP_2$, $SP_3$, and $SP_4$, respectively. Each of these SPs was calculated over a 1 ns MD trajectory for the RNA under conditions mentioned above. The moving averages were calculated over a window of 50 ps to filter out the coherent part of the variations from the fluctuations ($\lambda$). These fluctuations were calculated using:

$$\lambda(SP_j, t_i) = \frac{\sqrt{\sum_{i=0}^{N_f-1}[SP_j(t_i) - \langle SP_j \rangle]^2 / N_f}}{SP_{j,max}(t_i)}, \quad (17)$$

for j=1, 2, 3, 4, where $t_i$ is the $i^{th}$ time, $N_f$ is the total number of MD time frames used for the moving averages, $\langle SP_j \rangle$ is the moving average (over 50 ps), and $SP_{j,max}$ is the maximum absolute value of the SP within the range of SPs sampled for the moving average calculation. Fluctuations were defined about a moving absolute maxima rather than a moving average to avoid singularities for zero moving averages. The normalization makes $\lambda$ dimensionless. Thus $\lambda$ can be compared between different SPs and OPs. The time evolution of the dihedrals γ, δ and ϵ depends on their location in the back bone. δ fluctuates the least due to geometric constraints imposed by a five membered ring. In contrast, those not associated with the backbone fluctuate even more than γ or ϵ. Fluctuations of variables characterizing the overall size of the macromolecule, like $SP_2$ or $SP_3$, are much smaller. For $SP_4$, fluctuations are maximum, and are also sensitive to bond location.

The time evolution of these SPs was compared to that of the OPs described above. Fluctuations in $SP_1$ and $SP_4$ were several orders of magnitude higher in amplitude than those for the OPs, and/or their characteristic timescale was much shorter. Hence, they do not evolve slowly and cannot serve as a basis of a multiscale analysis. Finally, $SP_2$ and $SP_3$ are suitable as OPs but do not readily enable the generation of SP ensembles, as they are a subset of a more general set of OPs. This presents difficulties in computing thermal-average forces and diffusivities needed for a multiscale analysis. In contrast, the OPs described above are automatically generated, and therefore the set $\underline{\Phi}$ can be augmented for systems of higher complexity. Furthermore, the end-to-end distance and radius of gyration are accounted for via the more general OPs (as discussed below).

As system size increases, the OPs become better filters of the high frequency fluctuations. To validate this, heptaalanine with 8000 water molecules was simulated in a cubic box of side 44 Å, under settings set forth in Table I. Fluctuations in OPs for larger systems are found to be much smaller than those of smaller ones (i.e., the same OP shows amplified fluctuations as the system is changed from RNA to heptaalanine). Distinct differences in length scales allow better separation of the lower order OPs from those of the higher order ones in the RNA. This facilitates filtering of the low and high frequency modes. For smaller systems like heptaalanine, the length scale separation diminishes. In such situations, OPs cannot facilitate filtering of high frequency fluctuations, and consequently the implementation of multiscale analysis may become inefficient.

Figure 2A:
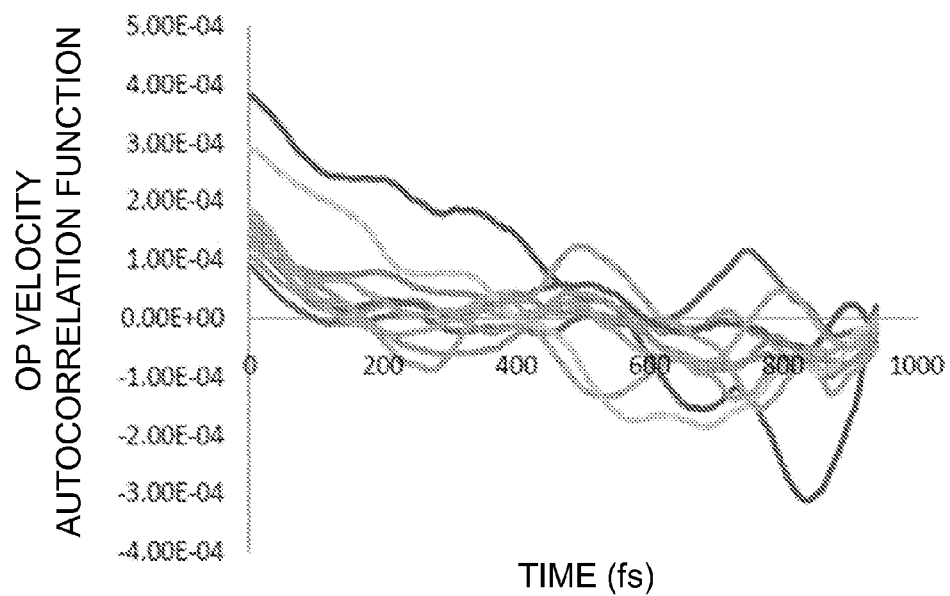
FIG. 2A is a diagram showing ten order parameter (OP) velocity auto-correlation function time-courses for 001Z starting from same initial conditions but different initial velocity random seeds.
Figure 2B:
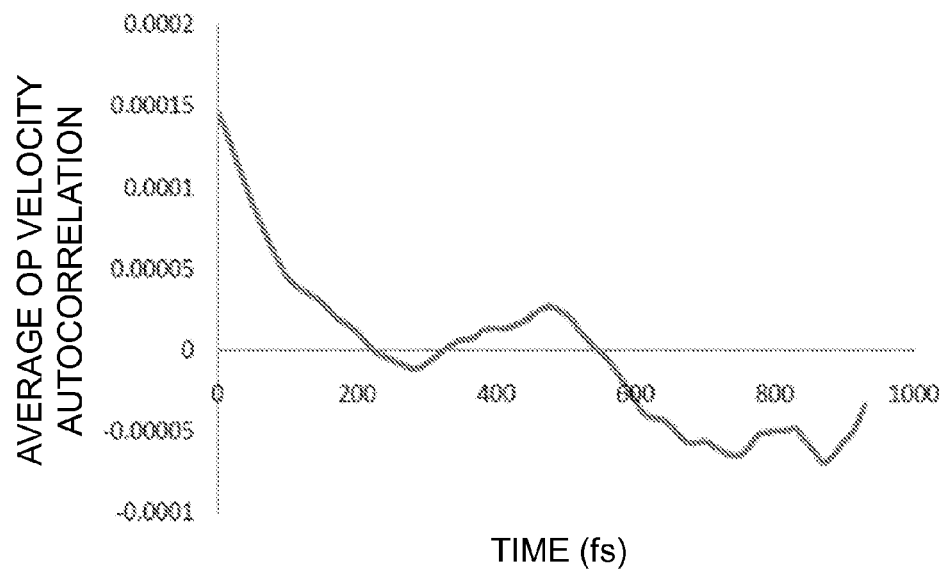
FIG. 2B is a diagram showing a Boltzmann average OP velocity auto-correlation function time-course, showing the absence of a long-time tail and a lack of coupling to other slow variables not included in a set of OPs.

The choice of OPs depends on the characteristics of the system of interest. This can be understood a priori via analyzing OP evolution for short MD trajectories and observing the decay in the OP velocity auto-correlation functions. It was found most efficient for the present problem to only use 4 OPs (i.e., the center of mass and 3 corresponding to overall extension-dilatation). To verify completeness of this set of OPs for the present problem, the OP velocity auto correlation functions were plotted for a window of 1 ps. The correlation decayed sharply on a timescale much shorter than that of OP evolution (i.e., the OPs were constant over the time of auto-correlation decay). The decay zone was followed by a fluctuating phase that reflects insufficient statistics for constructing long-time correlation function behavior. FIG. 2A illustrates a plot of several auto-correlation functions for 1 ps trajectories with identical starting structure and initial conditions but different random seeds for generating initial velocities. In principle, an average of such single MD simulation derived correlation functions is required to compute the diffusivities. However, using only the early part of a single MD correlation function (wherein the most statics are accumulated), as shown in FIG. 2B, was found to suffice. Furthermore, the correlation analysis validates the completeness of the set of OPs, as there is no long-time tail behavior in the correlation functions.

Omission of a slow variable that couples with the existing set can lead to a long-time correlation tail. To validate this, the correlation calculation was redone without the 100X OP. This led to a long-time tail in the velocity auto-correlation function for the 001Z and 010Y OPs. In general terms, the deformational behavior in a given Cartesian direction is driven by forces that depend on the OPs in all directions. Therefore, a missing OP will create an ensemble of atomic configurations that reflect its absence, which in turn is expressed in slower behavior of the retained OP velocities, and hence the associated auto-correlation functions. Simultaneously, the ensemble had a major population of structures with very high residuals (~10 Å), also signaling omission of a slow mode. Therefore, the diffusion calculation indicates the absence of a key slow variable that can be optimally added to the existing set via the procedure described above. Due to orthogonality of the basis functions described above, the cross-correlation functions between different OPs are several orders of magnitude smaller than the auto-correlation functions; this implies that the OPs are not coupled through the diffusivities, but only through the OP dependence of the thermal-average forces. This greatly simplifies the construction of the random forces as they are related to the diffusion matrix.

Constructing higher order OPs from an MD run via Eq. (4) shows that they are highly fluctuating and therefore not appropriate as OPs. Rather they are accounted for via the quasi-equilibrium probability density (i.e., in the ensemble used to calculate averages). As discussed above, the ensemble of atomistic configurations is generated via Eq. (2). The residuals ($\bar{\sigma}_i$) are generated by a formula similar in structure to that used to obtain the atomic positions, but the sum over basis functions do not include those associated with the OPs.

Addition of OPs to a pre-existing set is needed in various cases. If the system is changed (e.g., if it is composed of multiple macromolecules), then more OPs are required to form a complete set. The added OPs probe complex inter-macromolecular motions. New OPs could also be added in a dynamic fashion in the course of a simulation to account for types of motions absent initially. As mentioned above, the appearance of long-time tails in the correlation functions later in a simulation is a key indicator of the need to augment the set of OPs.

Figure 3A:
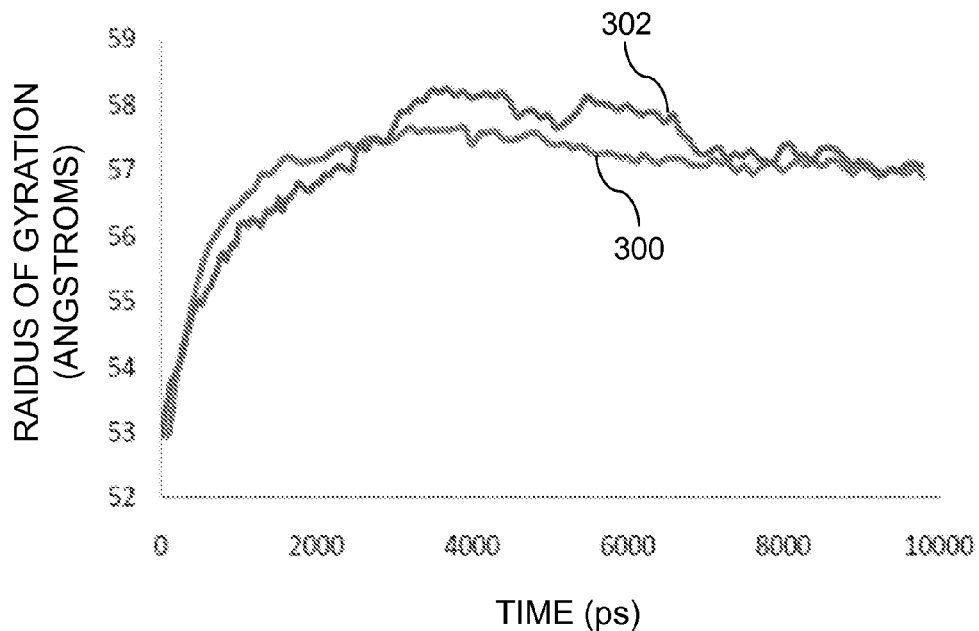
FIG. 3A is a diagram showing time evolution of a radius of gyration, generated using conventional MD and the presently disclosed DMS.
Figure 3B:
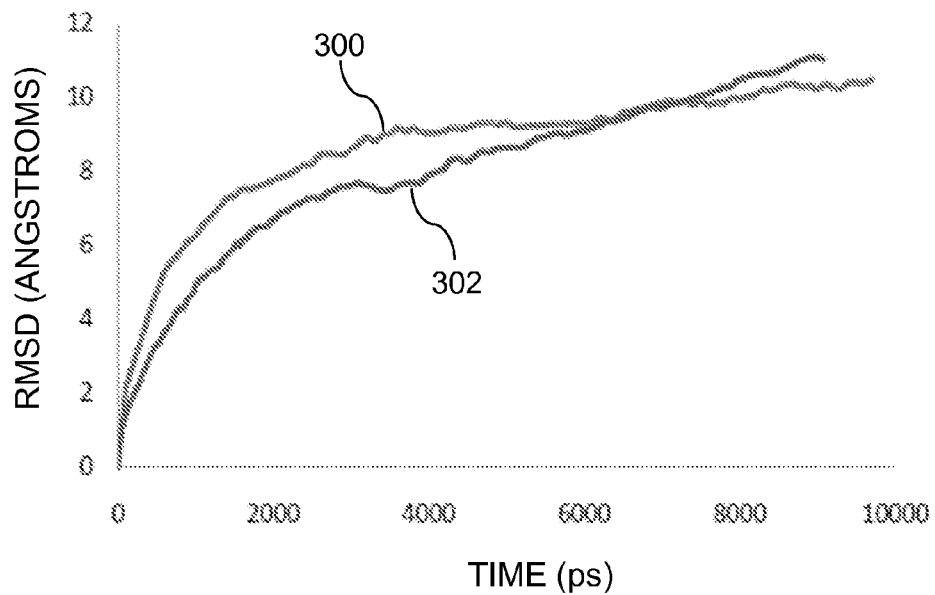
FIG. 3B is a diagram showing RMSD from a 0 ns structure to a 10 ns structure, generated using conventional MD and the presently disclosed DMS.
Figure 3C:
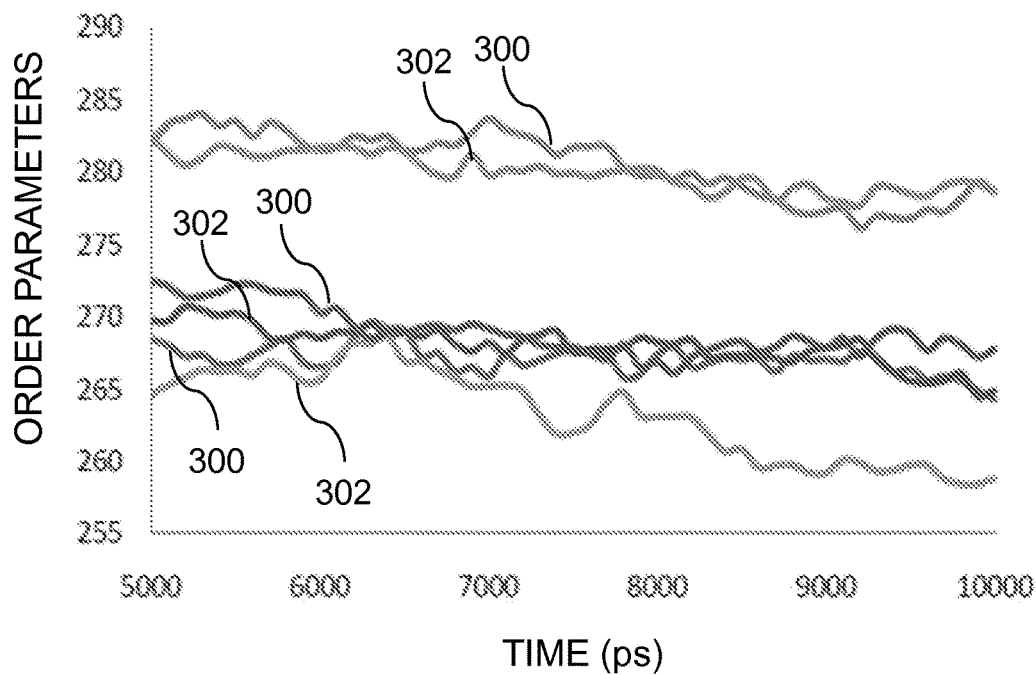
FIG. 3C is a diagram showing the values of OPs 010Y, 100X, and 001Z, generated using conventional MD and the presently disclosed DMS.
Figure 3D:
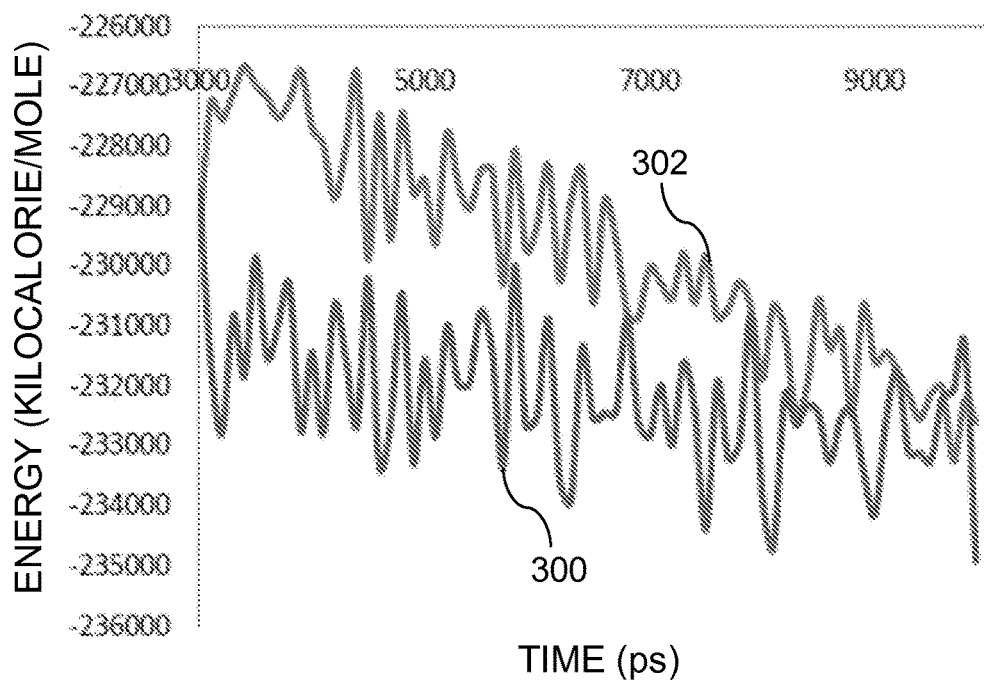
FIG. 3D is a diagram showing RNA potential energy, generated using conventional MD and the presently disclosed DMS.
Figure 3E:
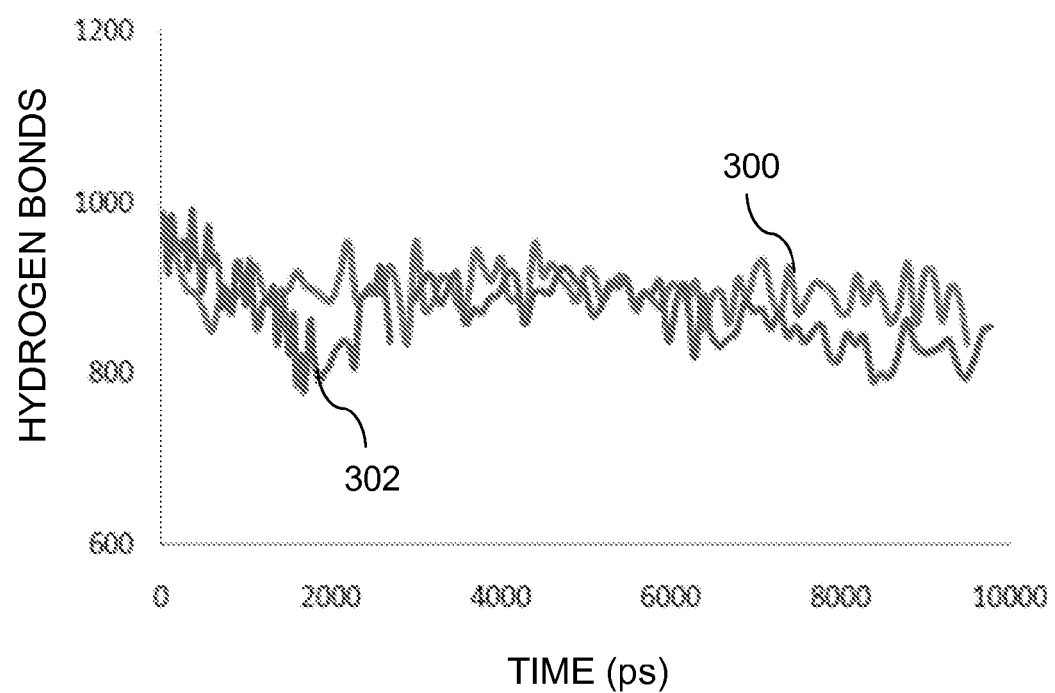
FIG. 3E is a diagram showing the number of nucleic acid-nucleic acid hydrogen bonds, generated using conventional MD and the presently disclosed DMS.

To assess the accuracy of the DMS, comparisons were carried out with conventional MD simulations for trajectories of 10 ns. On removal of the viral capsid, the RNA is no longer constrained and tends to expand. Following initial expansion, the RNA shrinks and finally fluctuates among a range of distinct atomistic states of similar energy. FIG. 3A shows the radius of gyration obtained with MD 300 and with the presently disclosed DMS 302, while FIG. 3B shows the progress of the RMSD from the initial structure as a function of time. Agreement of the radius and the RMSD between MD and the DMS is excellent. FIG. 3C plots OP time courses from the final 5 ns of conventional MD 300 and the DMS 302. These results show that both the structures are essentially a part of similar OP ensembles having similar overall characteristics, and confirm that the multiscale simulation is generating configurations consistent with the same value of the OPs that arise in MD. However, the multiscale simulation of the presently disclosed DMS actually corresponds to an ensemble of MD simulations (see below). Significantly, the multiscale simulation captures the overall structural dynamics, which is often the main interest. However, the atomistic configurations are also accounted for via the quasi-equilibrium distribution. This illustrates that radius of gyration and end-to-end distance (as mentioned above) is accounted for by the OPs. FIG. 3D shows the potential energy for the multiscale simulations, which fluctuates about a constant value. Energies show identical trend out to within a percent of those from the MD run. This shows that the RNA gains stability as the potential energy gradually decreases. Energies from the MD and the DMS generated trajectories 300, 302 show excellent agreement in trend as well as in magnitudes. The observed difference is within limits of those from multiple runs starting from the same initial structure with different initial velocities. As another basis of comparison, time evolutions of the number of intra-macromolecular hydrogen bonds for both methods are shown in FIG. 3E. Hydrogen bonds are defined solely on the basis of geometric parameters (bond angle: 20°; bond-length: 3.8 Å) between donors and acceptors. Initial expansion reduced the number of these bonds (primarily the ones involved in the RNA tertiary structure). The number of bonds decreased less rapidly in the later part of the trajectories when expansion ceased. A detailed account of the various types of hydrogen bonds is given below.

One advantage of multiscaling is the potential to use timesteps of tens or hundreds of picoseconds or greater (in contrast to the $10^{-15}$ sec of conventional MD). For relatively slow processes in large systems, this speed-up over conventional MD is significant. 128 processors were used to assess the efficiency of the presently disclosed DMS. During the initial transient, 40 ps timesteps were used. To accommodate the initial expansion and account for the structural anisotropy, the RNA was re-solvated in a bigger box (Table 1) after the first 3 ns. Post-initial transient, Langevin evolution was executed using 150 ps timesteps, reflecting the longer characteristic time for this phase. In this slower evolution regime (probed till 50 ns for the study), efficiency becomes 11 fold. However, comparison with a single MD run is not appropriate since the DMS corresponds to ensemble MD. In this study, a single DMS simulation corresponds to an ensemble of 168 traditional MD runs. While, for each MD run, the OP time-course is essentially the same as that predicted by the DMS, the detailed atomistic configuration varies dramatically among members of the ensemble. This factor of 168 comes from the sample size used in the Monte Carlo integration to compute the thermal-average forces. Finally, a single MD run may not be representative of an ensemble of possible time courses, which, in contrast, is automatically overcome in the presently disclosed DMS. If the finer short timescale structural transition is of interest, it can be pursued by either shorter timescale traditional MD runs or by including more OPs (although this will decrease the minimum characteristic time of OP dynamics and, therefore, reduce the efficiency of multiscale simulations). Selecting OPs for running the multiscale simulation involves an initial analysis of their time trends over the 1 ps to 1 ns timescale. However, this analysis need not be repeated in the course of simulations until the emergence of new OPs, thereby restoring efficiency to the multiscale simulation.

Figure 4:
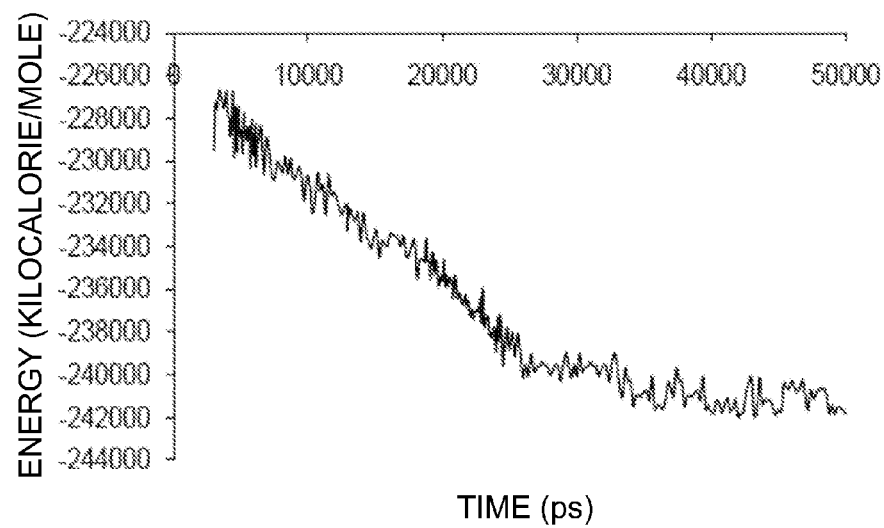
FIG. 4 is a diagram showing time evolution of the RNA potential energy via a 50 ns simulation, generated using the presently disclosed DMS.
Figure 5:
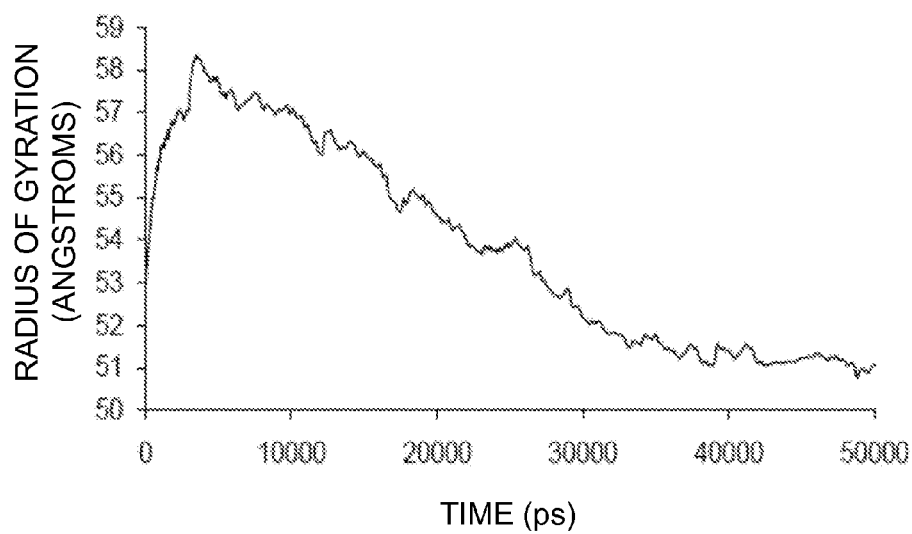
FIG. 5 is a diagram showing time evolution of the RNA radius of gyration via a 50 ns simulation, generated using the presently disclosed DMS.
Figure 6A:
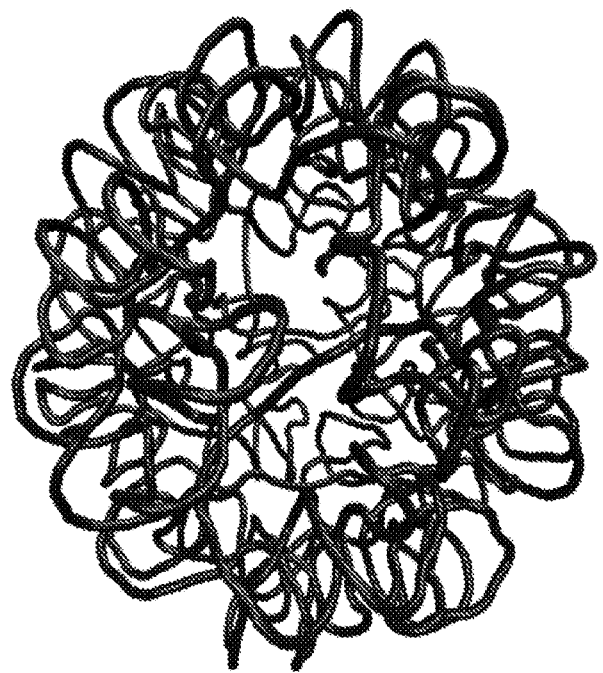
FIG. 6A is a simulated depiction of an illustrative RNA structure at 0 ns.
Figure 6B:
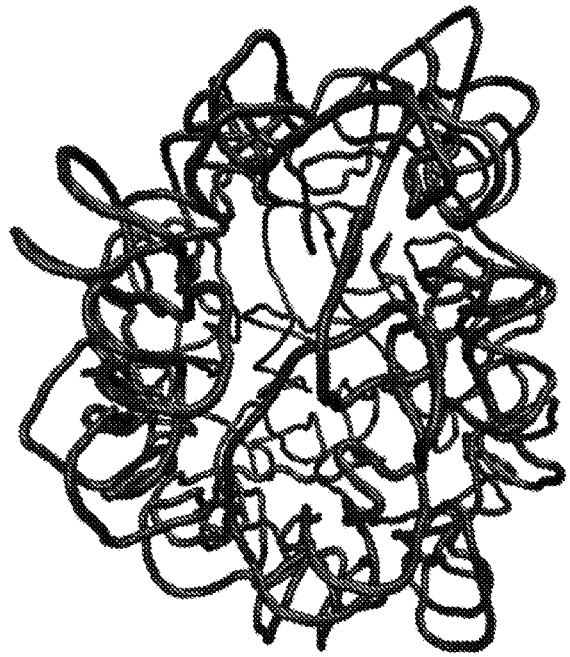
FIG. 6B is a simulated depiction of the illustrative RNA structure of FIG. 6A at 10 ns.
Figure 6C:
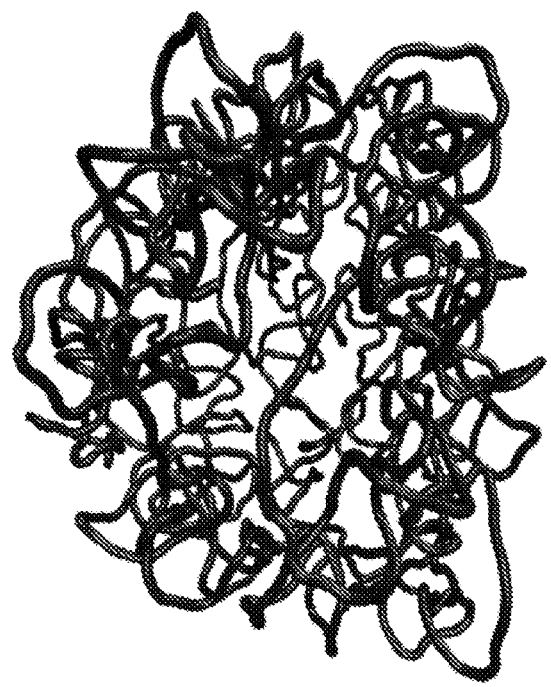
FIG. 6C is a simulated depiction of the illustrative RNA structure of FIG. 6A at 20 ns.
Figure 6D:
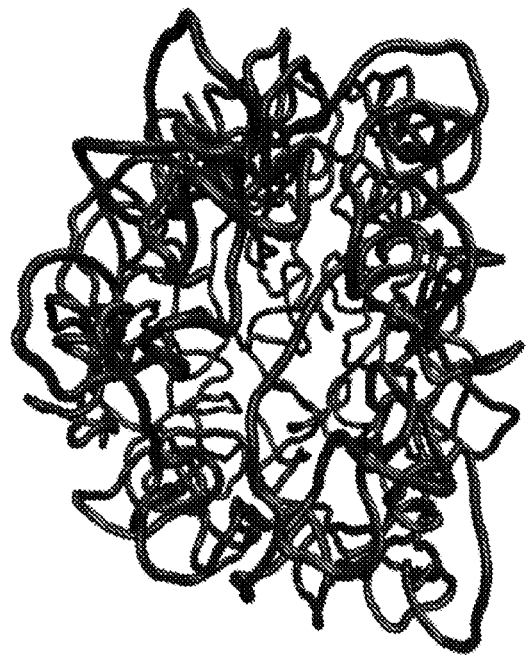
FIG. 6D is a simulated depiction of the illustrative RNA structure of FIG. 6A at 30 ns.
Figure 6E:
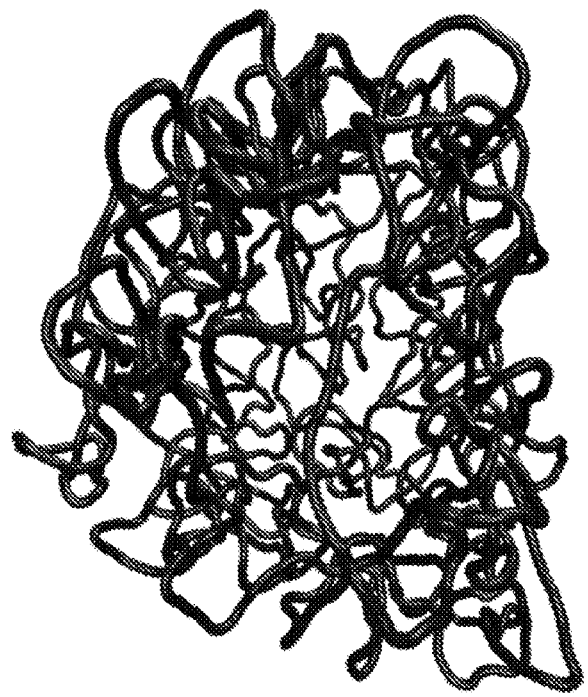
FIG. 6E is a simulated depiction of the illustrative RNA structure of FIG. 6A at 40 ns.
Figure 6F:
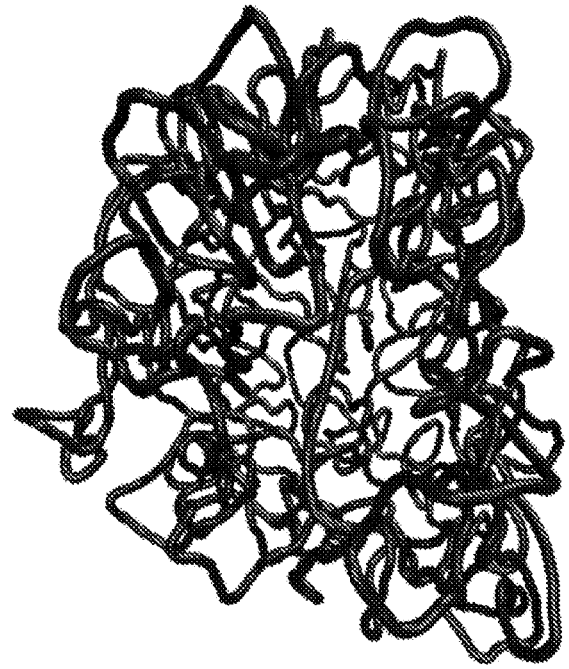
FIG. 6F is a simulated depiction of the illustrative RNA structure of FIG. 6A at 50 ns.
Figure 7:
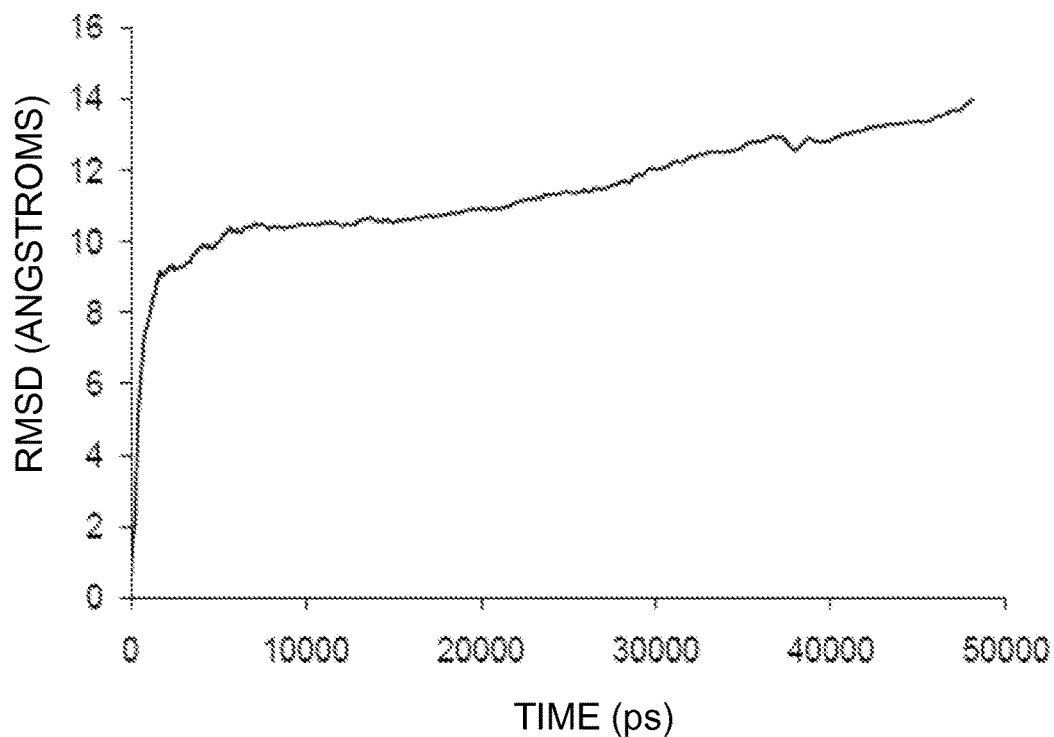
FIG. 7 is a diagram showing RMSD from a 0 ns structure to a 50 ns structure, generated using the presently disclosed DMS.

Making use of the above efficiency, the long-time behavior of the RNA was probed using the presently disclosed DMS. FIG. 4 shows a plot of potential energy versus time for the RNA. The energy decreases and fluctuates about a minimum. FIG. 5 shows a plot of the radius of gyration for the 50 ns trajectory. Following rapid initial expansion, RNA gradually shrinks for 30 ns before reaching a dynamic equilibrium, wherein it fluctuates about 50 Å. These overall changes in shape and size are tracked by the OPs. Their values also gradually decrease before flattening out. However, the magnitude of the three OPs is different, probing different extents of deformation along the three Cartesian axes. This is consistent with the fact that even though overall shape and size follow simple trends (reflected in FIG. 5), the anisotropy in the system leads to a symmetry breaking which is tracked by the OPs and the constant OP ensemble. FIGS. 6A-F validate that the initial symmetry is completely lost in the course of the simulation. In the final structure, shown in FIG. 6F (after 50 ns), the tertiary structure of the RNA is highly disrupted, though secondary structure still remains. The latter is in agreement with experiments that suggest free RNA can possess some secondary structure. FIG. 7 shows the RMSD over the entire 50 ns trajectory. RMSD shows a rapid increase followed by a gradual one. The increase in RMSD over the final 20 ns trajectory signifies that even though the energy, overall shape and size (OPs) change negligibly, there are local (non-coherent) changes that are accounted for by the constant OP ensemble (i.e., fluctuations in the higher order OPs). Thus, the presently disclosed DMS captures the exploration of multiple iso-energetic configurations by the RNA.

Figure 8:
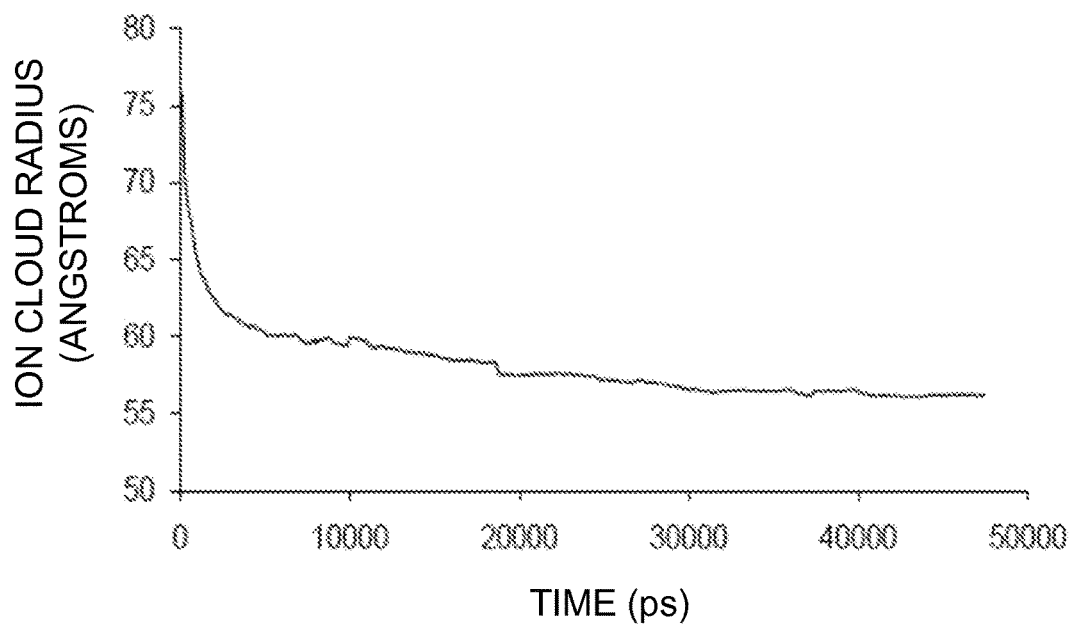
FIG. 8 is a diagram showing time evolution of a mobile ion (Na+) cloud radius over 50 ns.
Figure 9A:
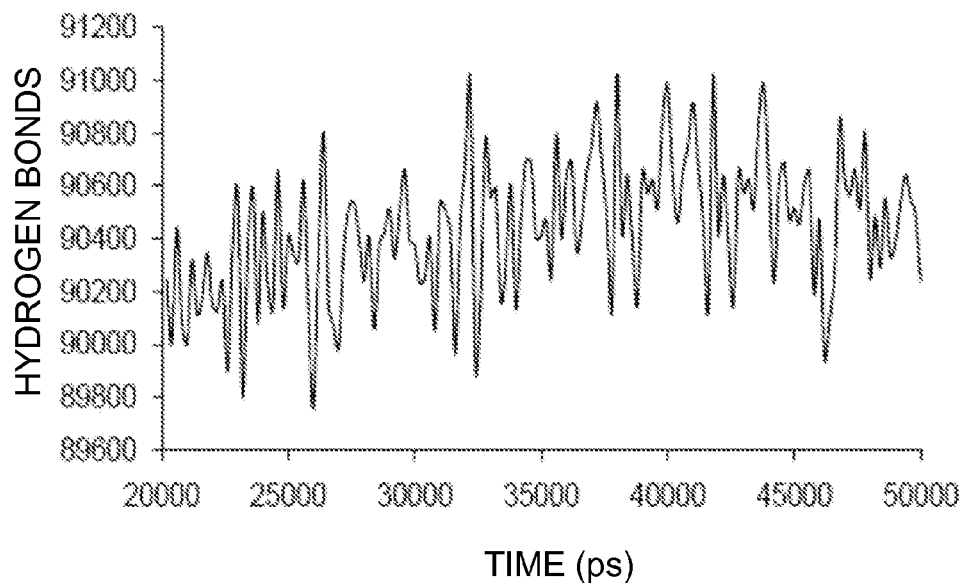
FIG. 9A is a diagram showing time evolution of the water-water hydrogen bonds for simulated RNA dynamics during the final 30 ns of the simulation of FIGS. 6A-F.
Figure 9B:
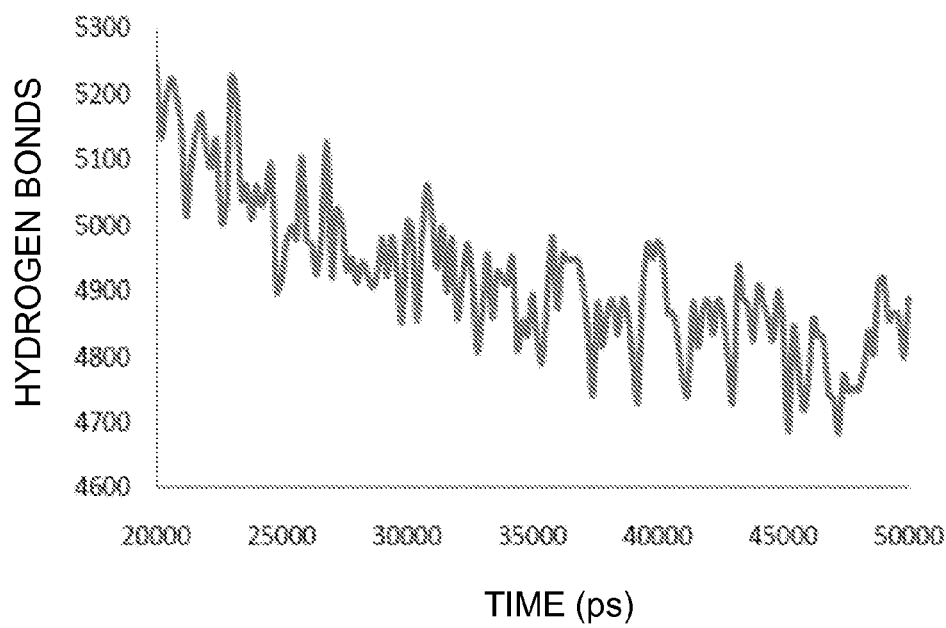
FIG. 9B is a diagram showing time evolution of the nucleic acid-water hydrogen bonds for simulated RNA dynamics during the final 30 ns of the simulation of FIGS. 6A-F.
Figure 10A:
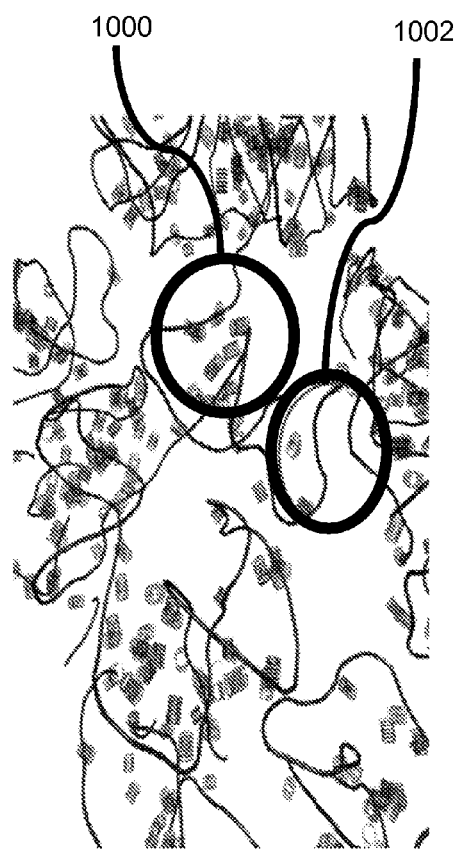
FIGS. 10A and 10B are simulated depictions showing a shift in hydrogen bonds from a first region in FIG. 10A to a second region in FIG. 10B.
Figure 10B:
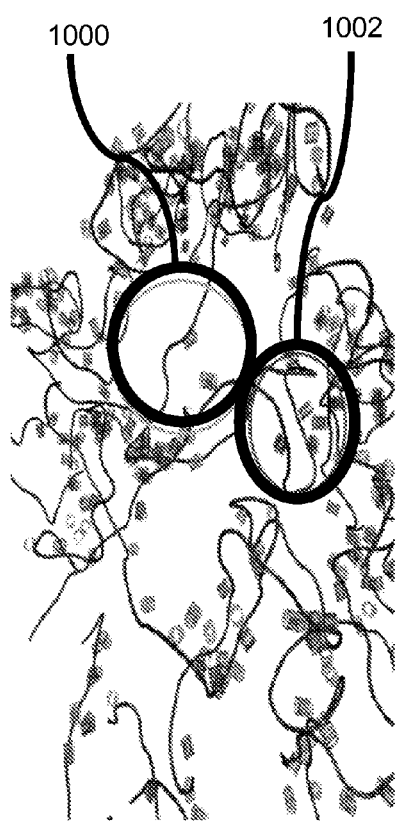
Figure 10C:
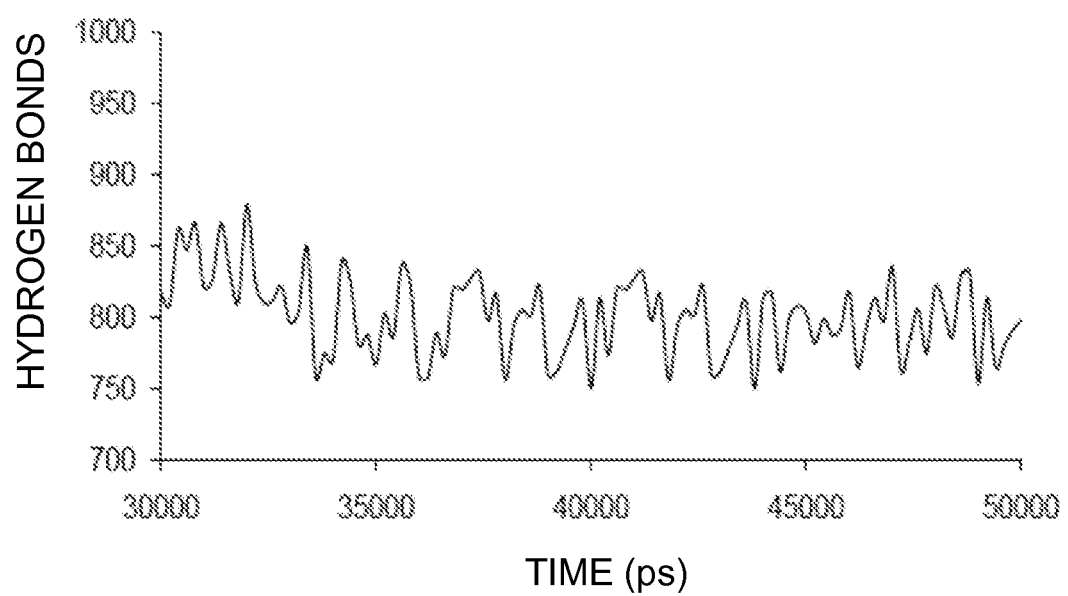
FIG. 10C is a diagram showing a time evolution of a number of nucleic acid-nucleic acid hydrogen bonds for the final 20 ns of the simulation of FIGS. 6A-F.

The gradual shrinkage of RNA is explained on the basis of ion shielding effects. FIG. 8 shows that the radius of the ion cloud decreases with time. Thus, the ion cloud concentrates and distributes about the RNA, shielding the electrostatic repulsion between similarly charged nucleic acid residues in the RNA, causing them to come closer. When the cloud is removed, similarly charged groups mutually repel, and the RNA expands instead of shrinking. To confirm the above physical picture, the structure at the end of 20 ns was de-ionized and a further 7.5 ns simulation was carried out in aqueous solvent. The expansion due to electrostatic repulsion was reflected in the radius of gyration and OP changes over this simulation. A 1:1 electrolyte was used since the ions are diffusively bound and exchange positions (unlike for tightly bound ions such as $Mg^{2+}$), justifying their inclusion as a part of the ensemble and not as an OP. Even though the ions are not included in an OP calculation, their rapid quasi-equilibrium redistribution accompanying structural changes in the OP defined macromolecule at each Langevin timestep correctly accounts for the ion cloud around the RNA. Closely related to the distribution of ions is the distribution of water and hydrogen bonds. The total number of hydrogen bonds remains constant throughout the 50 ns simulation. However, the number of nucleic acid-water hydrogen bond decreases, while those for water-water hydrogen bonds increases, conserving the total number of bonds, as shown in FIGS. 9A and 9B. This phenomenon is consistent with mobile ion screening induced RNA shrinkage. As the RNA shrinks, water from the inner RNA cavity is expelled, thereby increasing the number of bulk water-water interactions. These shifts in sodium ion population, coordinated with hydrogen bond rearrangement, guide the system to the final structure. There is also a re-distribution of inter-nucleotide hydrogen bonds as the RNA samples iso-energetic configurations in the final 20 ns. This shift in hydrogen bonds is shown between FIGS. 10A and 10B (from region 1000 to region 1002). However, the total number of nucleic acid-nucleic acid hydrogen bonds is conserved, as shown in the plot of FIG. 10C.

While coherent structural dynamics are tracked by changes in the OPs, additional high frequency macromolecular motions are captured by the residual modified/MD generated ensemble. These high frequency modes capture small-timescale local alterations, over and above the OP mediated deformations in the RNA, and consequent effects on atom scale features like the hydrogen bond distribution. However, other complex and/or slow modes like bending or twisting can arise in the course of the RNA dynamics and affect the hydrogen bonds. As stressed above, emergence of new modes can be captured by the OPs described above and are signaled by the self consistency checks. Within the simulated period of time (50 ns), no long-time velocity auto-correlation tails or significant populations of high residual structures signifying the absence of additional slow modes were detected. A plausible explanation is that in viral RNAs it is possible that the bending modes leading to an unfolding transition appear much later in the time course (>50 ns) of structural evolution or secondary structure disruption occurs at a temperature much higher than 300K.

Figure 11A:
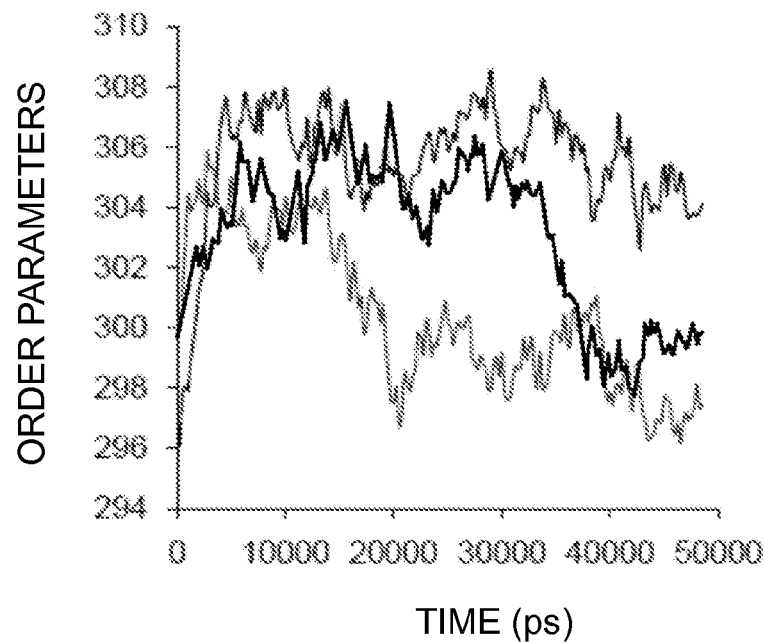
FIG. 11A is a diagram showing time evolution of OPs for a protein bound RNA in 0.3M NaCl solution at 300K.
Figure 11B:
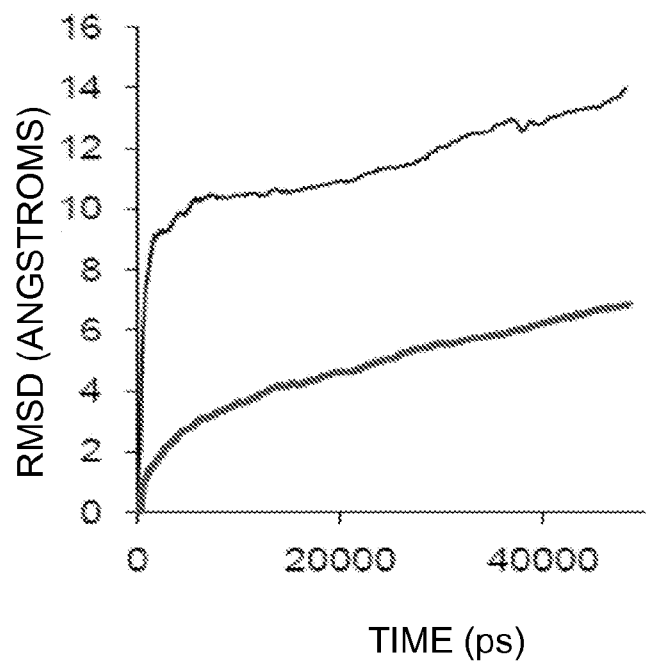
FIG. 11B is a diagram showing time evolution of RMSD for the protein bound RNA of FIG. 11A.
Figure 11C:
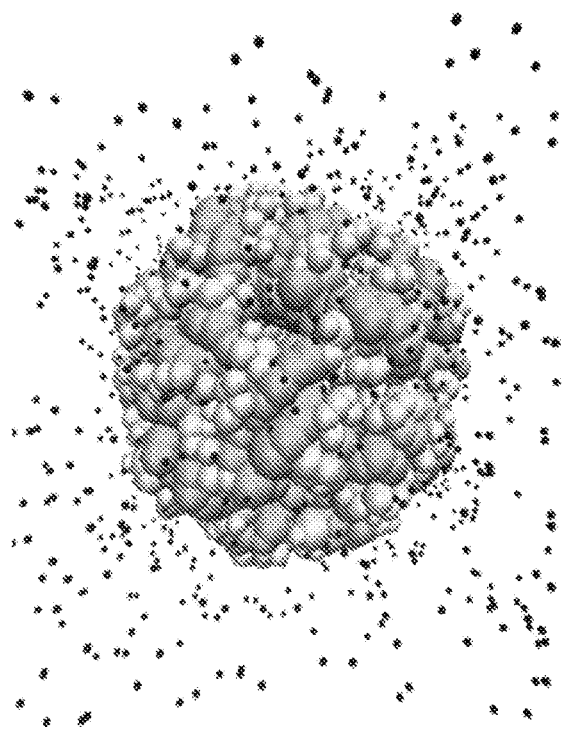
FIGS. 11C and 11D are simulated depictions of a structure for the protein bound RNA of FIG. 11A, showing restriction on RNA motion imposed by the proteins.
Figure 11D:
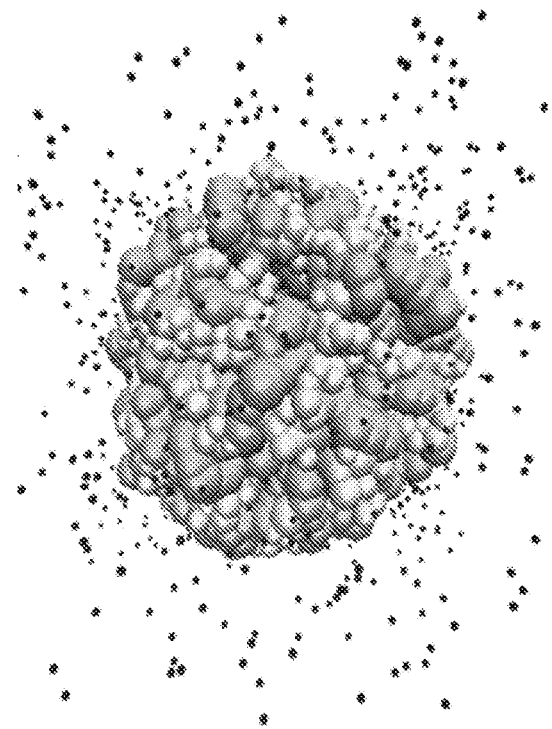

A control experiment was also performed to compare the deformation in the free RNA versus that in protein encapsulated RNA. The simulation was rerun using identical physical conditions (temperature, salinity) and software settings for the RNA core of STMV. The RNA core is composed of capsid protein strands (residue 2 to 27) complexed with the RNA. This complex is found to be stable with a radius distribution of ~50 Å. The added protein segments complex with the RNA, reducing the degrees of freedom. The structure was energy minimized and thermally equilibrated before starting the multiscale simulation. Time evolution of the OPs, the RMSD, and the structures for this simulation are shown in FIGS. 11A-D. FIG. 11B also shows the RMSD for free RNA. RMSD of RNA in the bound state is much less than in the free state. Unlike the previous case where the difference in the OPs was large, here the difference is small and their change is slower; this suggests the preservation of the symmetry originally imposed by the capsid. Thus, changes in the protein RNA complex are much less than those of free RNA. This longer characteristic time allows more efficient application of OP dynamics, as now timesteps of the order of 250 ps are possible. This implies that the presently disclosed DMS is 16 times faster than a single conventional MD for the present problem.

The simulations described above validate the presently disclosed DMS that probes the dynamics of macromolecules using OPs. The OPs are slowly varying and, hence, are well-suited as a basis of the multiscale algorithm. Completeness of a set of OPs may be determined by the shortness of correlation times relative to the characteristic time of OP evolution. Automated construction of order parameters enables efficient augmentation of the set of OPs to address incompleteness. The DMS results show excellent agreement with those from a conventional MD run. The DMS efficiency increases for larger systems undergoing slow transformations, as these allow significant length and timescale separation for the OPs to filter out the high frequency fluctuations from the coherent dynamics. Thus, OP mediated coarse-graining of the free-energy landscape allows for a Langevin timestep of a few hundred ps ($10^5$ times greater than conventional MD). The DMS predictions correspond to an ensemble of MD trajectories and, hence, are more statistically significant than results from a single MD run. Multiscale simulation via the OP description was found to capture significant structural details like ion screening, hydrogen bond rearrangement, and symmetry breaking transitions. In summary, the presently disclosed DMS is ideally suited for studying structural dynamics in large macromolecules and macromolecular complexes.

While the disclosure has been illustrated and described in detail in the drawings and foregoing description, such an illustration and description is to be considered as exemplary and not restrictive in character, it being understood that only illustrative embodiments have been shown and described and that all changes and modifications consistent with the disclosure and recited claims are desired to be protected.

What is claimed is:
1. A deductive multiscale simulation method comprising:
   (i) constructing a set of order parameters that model one or more structural characteristics of a macromolecule;
   (ii) simulating an ensemble of atomistic configurations for the macromolecule using instantaneous values of the set of order parameters;
   (iii) simulating thermal-average forces and diffusivities for the ensemble of atomistic configurations;
   (iv) evolving the set of order parameters via Langevin dynamics using the thermal-average forces and diffusivities; and
   (v) repeating steps (ii)-(iv) at each of a plurality of Langevin timesteps, wherein each of the plurality of Langevin timesteps is between 50 and 100 picoseconds.
2. The deductive multiscale simulation method of claim 1, wherein step (i) comprises constructing the set of order parameters using an all-atom reference structure for the macromolecule.
3. The deductive multiscale simulation method of claim 2, further comprising updating the all-atom reference structure to reflect a deformation of the macromolecule.
4. The deductive multiscale simulation method of claim 1, further comprising adding one or more new order param- eters to the set of order parameters in response to the presence of a long-time tail in a correlation function.

5. The deductive multiscale simulation method of claim 1, wherein step (ii) comprises determining a quasi-equilibrium probability distribution of the ensemble of atomistic configurations following from entropy maximization constrained to the instantaneous values of the set of order parameters.

6. The deductive multiscale simulation method of claim 1, wherein step (iii) comprises determining an inter-atomic force-field using at least one of Monte Carlo integration and molecular dynamics.

7. The deductive multiscale simulation method of claim 1, further comprising synthesizing the macromolecule modeled by the set of order parameters.

8. The deductive multiscale simulation method of claim 7, wherein the synthesized macromolecule comprises a nanomedical system.

9. One or more non-transitory computer readable media comprising a plurality of instructions which, when executed by one or more processors, cause the one or more processors to:
  (i) construct a set of order parameters that model one or more structural characteristics of a macromolecule;
  (ii) simulate an ensemble of atomistic configurations for the macromolecule using instantaneous values of the set of order parameters;
  (iii) simulate thermal-average forces and diffusivities for the ensemble of atomistic configurations;
  (iv) evolve the set of order parameters via Langevin dynamics using the thermal-average forces and diffusivities; and
  (v) repeat steps (ii)-(iv) at each of a plurality of Langevin timesteps, wherein each of the plurality of Langevin timesteps is between 50 and 100 picoseconds.

10. The one or more non-transitory computer readable media of claim 9, wherein the plurality of instructions cause the one or more processors to perform step (i), at least in part, by constructing the set of order parameters using an all-atom reference structure for the macromolecule.

11. The one or more non-transitory computer readable media of claim 10, wherein the plurality of instructions further cause the one or more processors to update the all-atom reference structure to reflect a deformation of the macromolecule.

12. The one or more non-transitory computer readable media of claim 9, wherein the plurality of instructions further cause the one or more processors to add one or more new order parameters to the set of order parameters in response to the presence of a long-time tail in a correlation function.

13. The one or more non-transitory computer readable media of claim 9, wherein the plurality of instructions cause the one or more processors to perform step (ii), at least in part, by determining a quasi-equilibrium probability distribution of the ensemble of atomistic configurations following from entropy maximization constrained to the instantaneous values of the set of order parameters.

14. The one or more non-transitory computer readable media of claim 9, wherein the plurality of instructions cause the one or more processors to perform step (iii), at least in part, by determining an inter-atomic force-field using at least one of Monte Carlo integration and molecular dynamics.

15. The deductive multiscale simulation method of claim 1, wherein each order parameter of the set of order parameters is associated with many atoms.

16. The deductive multiscale simulation method of claim 1, wherein each order parameter of the set of order parameters describe a nano-scale feature of the macromolecule.

* * * * *